(12) United States Patent
Liu et al.

(10) Patent No.: US 7,541,450 B2
(45) Date of Patent: Jun. 2, 2009

(54) LIGAND-DEPENDENT PROTEIN SPLICING

(75) Inventors: David R. Liu, Lexington, MA (US); Allen R. Buskirk, Provo, UT (US)

(73) Assignee: President and Fellows of Harvard College, Cambridge, MA (US)

( * ) Notice: Subject to any disclaimer, the term of this patent is extended or adjusted under 35 U.S.C. 154(b) by 281 days.

(21) Appl. No.: 11/688,073

(22) Filed: Mar. 19, 2007

(65) Prior Publication Data

US 2007/0264692 A1 Nov. 15, 2007

Related U.S. Application Data

(62) Division of application No. 11/093,808, filed on Mar. 30, 2005, now Pat. No. 7,192,739.

(60) Provisional application No. 60/557,865, filed on Mar. 30, 2004.

(51) Int. Cl.
*C07H 21/02* (2006.01)
*C12P 21/06* (2006.01)
*C12P 21/04* (2006.01)

(52) U.S. Cl. ..................... 536/23.1; 435/69.1; 435/69.7

(58) Field of Classification Search ................. None
See application file for complete search history.

(56) References Cited

U.S. PATENT DOCUMENTS

| 5,981,182 A | 11/1999 | Jacobs et al. |
| 7,192,739 B2 | 3/2007 | Liu et al. |
| 2004/0091966 A1 | 5/2004 | Zeidler et al. |

FOREIGN PATENT DOCUMENTS

| WO | WO 2005/098043 A2 | 10/2005 |
| WO | WO 2005/098043 A3 | 10/2005 |

OTHER PUBLICATIONS

Mootz, et al., J. of Am. Chem. Soc., 124: 9044-9045 (2002).
Perler, et al., Nucleic Acids Research, 30(1): 383-384 (2002).
Evans, et al., J. of Biological Chemistry, 274(26): 18359-18363 (1999).
Holford, et al., Structure, 6: 951-956 (1998).
Guo, et al., Science, 288: 2042-2045 (2000).
Lin, et al., J. Am. Chem. Soc., 125: 612-613 (2003).
Picard, Methods Enzymol., 327: 385-401 (2000).
Clackson, Curr. Opin. Chem. Biol., 1: 210-218 (1997).
Gossen, et al., Science, 268:1766-1769, 1995.
Mootz, et al., J. of Am. Chem. Soc., 125: 10561-69, 2003.
Paulus, Annu. Rev. Biochem., 69: 447-496 (2000).
Pryciak, et al., Mol. Cell. Biol., 16: 2614-26 (1996).
Cadwell, et al., PCR Methods Appl., 2: 28 (1992).
Feil, et al., Proc. Natl. Acad. Sci. USA, 93: 10887-10890 (1996).
Mumberg, et al., Gene, 156: 119-122 (1995).
Daugelat, et al., Protein Sci., 8: 644-653 (1999).
Ozawa, et al., Anal. Chem., 73: 5866-5874 (2001).
Crameri, et al., Nat. Biotechnol., 14: 315-319 (1996).
Ormo, et al., Science, 273: 1392-1395 (1996).
Cormack, et al., Gene, 173: 33-38 (1996).
Mumberg, et al., Nucleic Acids Res., 22: 5767-5768 (1994).
Juers, et al., Protein Sci., 9: 1685-1699 (2000).
Mathews, et al., Struct. Fold. Des., 7: 1395-1406 (1999).
Cadwell, et al., PCR Methods Appl., 3: S136-S140 (1994).
Wood, et al., Nat. Biotechnol., 17: 889-892 (1999).
White, et al., EMBO J., 16: 1427-1435 (1997).
Shiau, et al., Cell, 95: 927-937 (1998).
Nichols, et al., EMBO J., 17: 765-773 (1998).
Ding, et al., J. Biol. Chem., 278: 39133-39142 (2003).
Prodromou, et al., Cell, 90: 65-75 (1997).
Alaimo, et al., Curr. Opin. Chem. Biol., 5: 360-367 (2001).
Siegele, et al., Proc. Natl. Acad. Sci. USA, 94: 8168-8172 (1997).
Pratt, et al., Endocr. Rev., 18: 306-360, (1997).
Buskirk, et al., PNAS, 101(29): 10505-10510 (2004).
Doyon, et al., J. Am. Chem. Soc., 125: 12372 (2003).
Gartner, et al., J. Am. Chem. Soc., 123: 6961 (2001).
Gartner, et al., Angew. Chem. Int. Ed., 41: 1796 (2002).
Gartner, et al., J. Am. Chem. Soc., 124: 10304 (2002).
Gartner, et al., Angew. Chem. Int. Ed., 42: 1370 (2003).
Hall, et al., J. Mol. Biol. 323: 173 (2000).
Lew, et al., Gene 282: 169-177 (2002).
Li, et al., J. Am. Chem. Soc. 125: 10188 (2003).
Luque, et al., Proteins Suppl. 4: 63 (2000).
Rosenbaum, et al., J. Am. Chem. Soc. 125: 13924 (2003).
Shingledecker, et al., Gene 207: 187-195 (1998).
Taylor, et al., Angew. Chem. Int. Ed. 40: 3310-3335 (2001).
White, et al., EMBO Journal 20(18): 5207-5218 (2001).
Creighton, 2d. ed. W.H. Freeman and Co., 255-256 (1992).
International Search Report, PCT/US05/10805, date of mailing Nov. 8, 2006.
Written Opinion of International Searching Authority, PCT/US05/10805, date of mailing Nov. 8, 2006.

*Primary Examiner*—Suzanne M. Noakes
(74) *Attorney, Agent, or Firm*—Choate, Hall & Stewart LLP; C. Hunter Baker; K. Nicole Clouse

(57) ABSTRACT

Ligand-dependent inteins allow for modulation of a protein's activity in vivo. Upon binding of the ligand to the ligand-dependent intein inserted into the protein of interest, the hybrid protein undergoes protein splicing removing the intein. The activity of the spliced protein is then restored. A 4-hydroxytamoxifen-dependent intein based on the *M. tuberculosis* RecA intein is prepared and demonstrated in a variety of exteins contexts. The invention provides a system for engineering other ligand-dependent inteins and using them, including the ligand-dependent inteins themselves, hybrid proteins with the inserted ligand-dependent inteins, polynucleotides encoding inteins and hybrid proteins, and engineered cells. Kits with the materials and reagents necessary for preparing and using ligand-dependent inteins are also included.

25 Claims, 26 Drawing Sheets

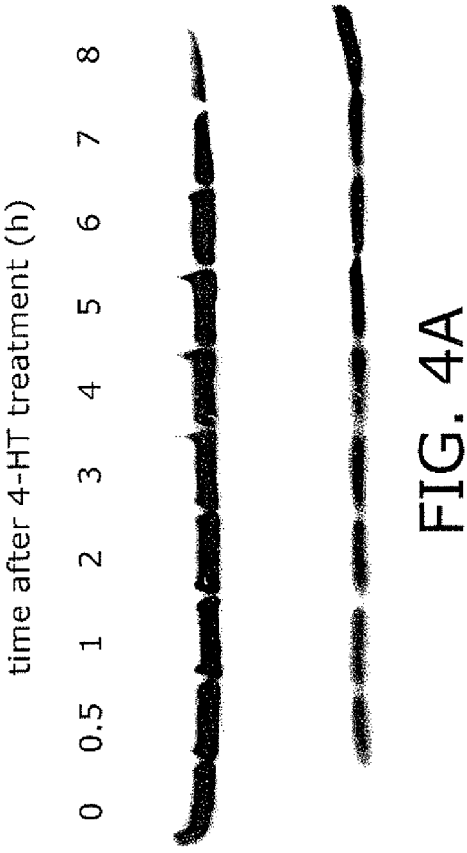
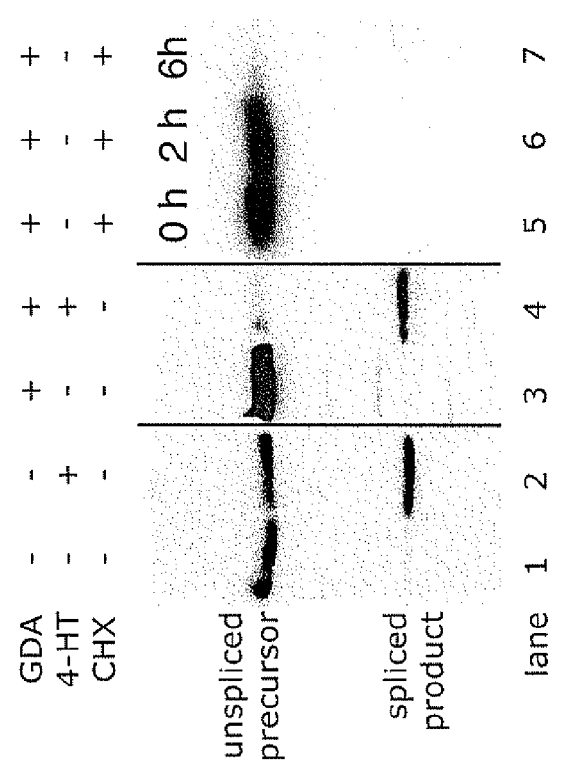
FIG. 4A
FIG. 4B
FIG. 4C

KanR(N)-wt intein-KanR(C)
150 μg/mL geneticin

Kan(R)-Cys>Ala intein-KanR(C)
150 μg/mL geneticin

KanR(N)-intein(N)-ER-LBD-intein(C)-KanR(C)
no 4-HT
no geneticin
(plating control)

10 μM 4-HT
150 μg/mL geneticin no 4-HT
150 μg/mL geneticin

Round 3 Evolves Highly Ligand-Dependent and More Active Inteins

| round-clone # | ER-LBD mutations | intein mutations |
|---|---|---|
| 1-1 | - | V67L |
| 1-5 | V533E, Y537H | - |
| 1-14 | V376A, R521G | - |
| 1-16 | V376A | K394R, L396Q |
| 2-4 | R335S, C530Y, V478A, V376A, R521G | H41L |
| 2-5 | S468P, V376A, R521G | V31M, R416L |
| 3-2 | R335S, C530Y, V478A, V376A, R521G, K531T | A34V, H41L |

FIG. 19

Evolution Ancestry of Intein 3-2

| round-clone# | ER mutations | intein mutations |
|---|---|---|
| 1-14 | V376A, R521G | - |
| 2-4 | R335S, C530Y, V478A, V376A, R521G | H41L |
| 3-2 | R335S, C530Y, V478A, V376A, R521G, K531T | A34V, H41L |
| minimal 3-2 | V376A, R521G | A34V, H41L |

Generality of an Evolved Protein Switch

Generality of an Evolved Protein Switch

Generality of an Evolved Protein Switch

LIGAND-DEPENDENT PROTEIN SPLICING

RELATED APPLICATIONS

The present application is a divisional of and claims priority under 35 U.S.C. § 120 to U.S. application Ser. No. 11/093,808, filed Mar. 30, 2005, now U.S. Pat. No. 7,192,739; which claims priority under 35 U.S.C. § 119(e) to U.S. provisional patent application Ser. No. 60/557,865, filed Mar. 30, 2004, entitled "Small Molecule-Dependent Protein Splicing"; the entire contents of each of which is incorporated herein by reference.

GOVERNMENT SUPPORT

The work described herein was supported, in part, by a grant from the National Institutes of Health/National Institute of General Medical Sciences (R01GM065400). The United States government may have certain rights in the invention.

BACKGROUND OF THE INVENTION

Biological systems use ligand-dependent proteins and nucleic acids as molecular switches to transduce inputs into appropriate cellular responses. For example, the activity of many enzymes is regulated by the presence of allosteric effectors. Artificial molecular switches are of particular interest (Guo et al. *Science* 288:2042-2045, 2000; Lin et al. *J. Am. Chem. Soc.* 125:612-613, 2003; Picard, *Methods Enzymol.* 327:385-401, 2000; Clackson, *Curr. Opin. Chem. Biol.* 1:210-218, 1997; Gossen et al. *Science* 268:1766-1769; each of which is incorporated herein by reference), because they enable biological functions to be controlled by small molecule inputs chosen by the researcher rather than by nature.

Protein-splicing elements, termed inteins, can mediate profound changes in the structure and function of proteins. Inteins are analogous to the introns found in polynucleotides. During intein-mediated protein splicing, the intein is present in the mature mRNA and translated to form the precursor protein. Inteins catalyze both their own excision from within a polypeptide chain and the ligation of the flanking external sequences (exteins) resulting in the formation of the mature protein from the exteins, and the free intein. No natural inteins, however, have been shown to be regulated by small molecules. Extein function is typically disrupted by the presence of an intein but restored after protein splicing. Many inteins can splice in foreign extein environments. Therefore, inteins are powerful starting points for the creation of artificial molecular switches.

Muir and coworkers (Mootz et al. *J. Am. Chem. Soc.* 124:9044-45, 2002; Mootz et al. *J. Am. Chem. Soc.* 125:10561-69; each of which is incorporated herein by reference) recently described the fusion of the N- and C-terminal halves of the *Saccharomyces cerevisiae* VMA intein with the FKBP and FRB proteins, creating rapamycin-dependent splicing in trans. Modulation of protein function, however, has not yet been reported using the resulting split inteins, and their application may be limited by the instability of partially folded, split proteins.

A ligand-dependent intein on a single polypeptide chain that can be used to modulate the function of a target protein has yet to be generated. Such an intein could preferably be used in a variety of target proteins, thereby making such an intein very useful in elucidating the functions of various target proteins in vivo.

SUMMARY OF THE INVENTION

Ligand-dependent inteins represent attractive molecular switches because they can be inserted into any protein of interest to render protein function dependent on the ligand. Because ligand splicing is rapid (Paulus, *Annu. Rev. Biochem.* 69:447-496, 2000; incorporated herein by reference) as compared to transcription and translation, the accumulated, unspliced protein may be activated after addition of the ligand effector on time scales that cannot be achieved by activating transcription or translation. In addition, this post-translational activation may depend on the concentration of the ligand added. A single ligand-dependent intein may be used in a multitude of proteins without requiring the engineering of a specific ligand-dependent intein for each protein. That is, a single ligand-dependent intein can regulate any protein without requiring the discovery of a specific activator for each protein of interest. Therefore, ligand-dependent inteins combine the advantages of small molecule chemical genetics with the target specificity and generality of classical genetics.

Although ligand-dependent inteins are promising tools for studying biology and treating disease, natural inteins are not regulated by ligand binding, instead splicing spontaneously after translation and protein folding. Ligand-dependent inteins preferably (1) bind a ligand with adequate affinity and specificity, and (2) transduce ligand binding into conformational changes that initiate protein splicing. The first aspect of ligand-dependent inteins may be accomplished by incorporating known ligand binding protein domains into natural inteins. This aspect may also be accomplished by protein engineering or design based on information in the art, or it may be accomplished by molecular evolution in which libraries of candidate proteins are selected and screened for ligand binding. The second aspect may be accomplished by molecular evolution in which intein libraries are selected and screened for ligand-dependent function or by rational design based on information in the art such as protein sequences and structural data. The strategy of using molecular evolution is particularly attractive since the complexity of propagating conformational changes within a protein makes the rational engineering of ligand dependent protein splicing extremely difficult.

The invention provides ligand-dependent inteins and hybrid proteins which include ligand-dependent inteins. These inteins typically include a ligand binding domain inserted into a natural intein. The inteins have been evolved or engineered to transduce ligand binding into protein splicing yielding a functional, spliced mature protein. The ligand-dependent intein may be inserted into the sequence of a protein of interest whose activity is to be modulated. The intein may be inserted anywhere in the protein of interest; however, insertion into α-helical domains or β-strands is particularly useful. In some embodiments, the activity of the protein of interest is disrupted upon insertion of the intein into its native structure. Therefore, insertion into domains where the intein breaks up secondary, tertiary, or quaternary structure is desired. Upon insertion of the intein into the protein, the ligand binding domain should retain the ability to binds its ligand with high affinity and specificity. In some cases, binding of the ligand to the intein causes a conformational change allowing for spontaneous excision of the intein, thereby restoring protein function. According to the present invention, any protein whose activity can be disrupted and restored by insertion and excision of an inventive ligand-dependent intein can be utilized. A few examples of proteins that can be used in the invention include enzymes (e.g., aminoglycoside phosphorylase, β-galactosidase, Ade2p)), fluorescent proteins (e.g., green fluorescent protein), transcription factors (e.g., Gli1 and Gli3 transcription factors of the Hedgehog pathway), cell signaling proteins (e.g., Smoothened), structural proteins, protein or peptide hormones, and cytokines.

In certain embodiments, the ligand binding domain binds a small molecule. In some cases, the ligand binding domain is the ligand binding domain of a known receptor protein. For example, the ligand binding domain of the estrogen receptor, which is known to bind the small molecule 4-hydroxy-tamoxifen (4-HT), may be used in an inventive intein. As would be appreciated by those of skill in this art, almost any ligand binding domain may be used in a ligand-dependent intein. The ligand may be a small molecule, a polynucleotide, a peptide, a protein, amino acid, etc. Preferably, the ligand is cell permeable.

Any intein may be engineered and/or evolved into a ligand-dependent intein. Preferably, the native intein can efficiently splice itself from a wide variety of extein contexts. In one embodiment, the *Mycobacterium tuberculosis* RecA intein is used. A list of inteins is found in the intein database InBase (Perler, F. B. (2002). InBase, the Intein Database. *Nucleic Acids Res.* 30:383-384; incorporated herein by reference). Any of the inteins listed in the database may be made into ligand-dependent inteins.

The invention also provides polynucleotides encoding the ligand-dependent inteins as well as polynucleotides encoding hybrid proteins, which comprise ligand-dependent inteins inserted into proteins of interest. These polynucleotides may be in the form of vectors for transforming cells. The invention also provides cells transformed with polynucleotides encoding ligand-dependent inteins or hybrid proteins. In certain embodiments, the cells are bacterial cells (e.g., *E. coli*), yeast cells (e.g. *Saccharomyces cerevisiae*), or mammalian cells (e.g. human, rat, mouse).

In another aspect, the invention provides a method of preparing ligand-dependent inteins. The method begins with adding a ligand binding domain to a known intein sequence. In certain instances, the addition of a ligand binding domain can be accomplished by inserting a ligand binding domain into an intein sequence. In other embodiments, an intein may be evolved to contain a ligand binding domain. This addition of a ligand binding domain may be accomplished using any techniques for preparing recombinant DNA molecules. The intein is then inserted in frame into an open reading frame of a protein of interest to create a hybrid protein. The insertion of the intein should disrupt or reduce the activity of the protein of interest. In certain embodiments, the activity of the protein of interest is easily determinable. For example, the growth of a cell may depend upon the activity of the protein, or the protein may have a physical property such as fluorescence making it easily detectable. The intein portion of the construct is then mutated (e.g., by error-prone PCR) to create a library of possible inteins in the protein of interest. The resulting inteins are assayed for splicing with and without the ligand being present (e.g., negative and positive selection; negative and positive screening). Preferably, there is minimal to no splicing if the ligand is not present, and increased splicing, preferably 5×, 10×, 100×, 1000×, when the ligand is present. Inteins with minimal background splicing and ligand-dependent splicing are then selected. The selected inteins may be characterized and/or mutated and put through another round of positive and/or negative screening or selection. In certain embodiments, the intein is screened and/or selected for use in multiple extein contexts. Once an intein of sufficient ligand dependency and minimal background splicing is discovered, it may be inserted into other proteins of interest for use. Therefore, a ligand-dependent intein may be designed once and then used in a variety of proteins for research or therapeutic purposes.

The invention provides using the discovered inteins by inserting them into a protein of interest whereby the activity of the protein of interest is modulated by the presence of the ligand. In certain embodiments, the protein's activity is modulated in a concentration dependent manner. Once the construct encoding the protein with the intein is introduced into a cell, the activity of the protein may be regulated by the addition of the ligand to the cell. The method is particularly useful in understanding the protein's role in the cell and could also be used to treat disease (e.g., the activity of a protein may turned on at a particular time, or in a particular tissue or organ based on the presence of a ligand). The ligand may be provided exogenously or endogenously.

Kits are also provided for the practice of the invention. The kits may include polynucleotides encoding ligand-dependent inteins. The inteins may or may not be inserted into particular proteins. The kits may also include enzymes, buffers, cells, polynucleotides, vectors, primers, nucleotides, ligands, media, tubes, instructions, etc. Preferably, the kit is conveniently packaged for use in a laboratory setting. In certain embodiments, a researcher may use the kit to insert a ligand-dependent intein into a protein the researcher is interested in studying. The engineered protein may then be tested for modulation of activity by the ligand. Optionally, the ligand-dependent intein in the extein context may be further evolved. The protein with the ligand-dependent intein inserted may be used to understand the protein's role in the cell or the biochemical pathway the protein is in. In certain embodiments, the kit is provided for therapeutic purposes. For example, the kit may be used to design and/or evolve a therapeutic construct which is then introduced into a subject or cells of the subject, which then may be introduced into the subject. The cells may preferably be blood cells, bone marrow cells, stem cells, or progenitor cells. The kit may also include a vector for introducing the construct into cells.

DEFINITIONS

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

"Antibody": The term "antibody" refers to an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE.

"Effective amount": In general, the "effective amount" of an active agent refers to the amount necessary to elicit the desired biological response. As will be appreciated by those of ordinary skill in this art, the effective amount of a hybrid protein, a polynucleotide, or pharmaceutical composition may vary depending on such factors as the desired biological endpoint, the agent to be delivered, the disease or condition being treated, etc.

"Exteins": An "extein" is a polypeptide that is spliced together with another extein during protein splicing. Typically, an intein is flanked by two extein sequences that are ligated together when the intein catalyzes its own excision. Exteins are analogous to exons found in mRNA.

"Hybrid protein": A "hybrid protein" is a protein which has had a ligand-dependent intein inserted into its polypeptide chain. This may be accomplished by inserting a polynucleotide encoding a ligand-dependent intein into the open reading frame of the protein. In certain embodiments, the presence of the intein in the hybrid protein reduces or eliminates the activity of the protein. A hybrid protein may be created from any target protein by inserting a ligand-dependent intein. In certain embodiments, the target protein's activity is being studied using the inventive technology. In other embodiments, the hybrid protein is a therapeutic agent.

"Intein": An "intein" is a polypeptide that, in the proper extein context, will catalyzes its own excision from a larger polypeptide and ligation of the resulting ends. Inteins are analogous to the introns found in mRNA. The intein may catalyze protein splicing in a variety of extein contexts. An intein may be naturally occurring or be engineered or evolved.

"Ligand binding domain": A "ligand binding domain" is any protein sequence that binds a ligand. Typically, the properly folded domain binds the ligand. Preferably, the ligand binding domain can be inserted into a variety of polypeptide contexts and still retains its ability to bind its ligand. The ligand binding domain may be naturally occurring such as the ligand binding domain of the estrogen receptor or the antigen binding region of an antibody. The ligand binding domain may also be engineered, selected screened, or evolved by the hand of man. The ligand may be any chemical compound; however, small molecules, peptides, proteins, protein domains, polynucleotides, amino acids, nucleotides, nucleosides, natural produces, metabolites, and other biomolecules are preferred. Preferably, the domain binds its ligand with specificity and high affinity.

"Peptide" or "protein": According to the present invention, a "peptide" or "protein" comprises a string of at least three amino acids linked together by peptide bonds. The terms "protein" and "peptide" may be used interchangeably. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification (e.g., alpha aminadation), etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In certain embodiments, the modifications of the peptide lead to a more biologically active peptide.

"Small molecule": The term "small molecule," as used herein, refers to a non-peptidic, non-oligomeric organic compound either prepared in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. In certain other preferred embodiments, natural-product-like small molecules are utilized.

"Transformation": The term "transformation" as used herein refers to introducing a vector comprising a nucleic acid sequence into a host cell. The vector may integrate itself or a portion of itself into the chromosome of the cells, or the vector may exist as a self-replicating extrachromosomal vector. Integration is considered in some embodiments to be advantageous since the nucleic acid is more likely to be stably maintained in the host cell. In other embodiments, an extrachromosomal vector is desired because each host cell can contain multiple copies of the vector.

BRIEF DESCRIPTION OF THE DRAWING

FIG. 4 shows properties of evolved intein 3-2. (A) Genomically integrated GFP disrupted with intein 3-2 (intein 3-2-GFP) was expressed in the absence of 4-HT for 16 hours to accumulate unspliced protein. One hour after cycloheximide (100 µg/ml) was added to inhibit new protein synthesis, 10

Figure 2A:
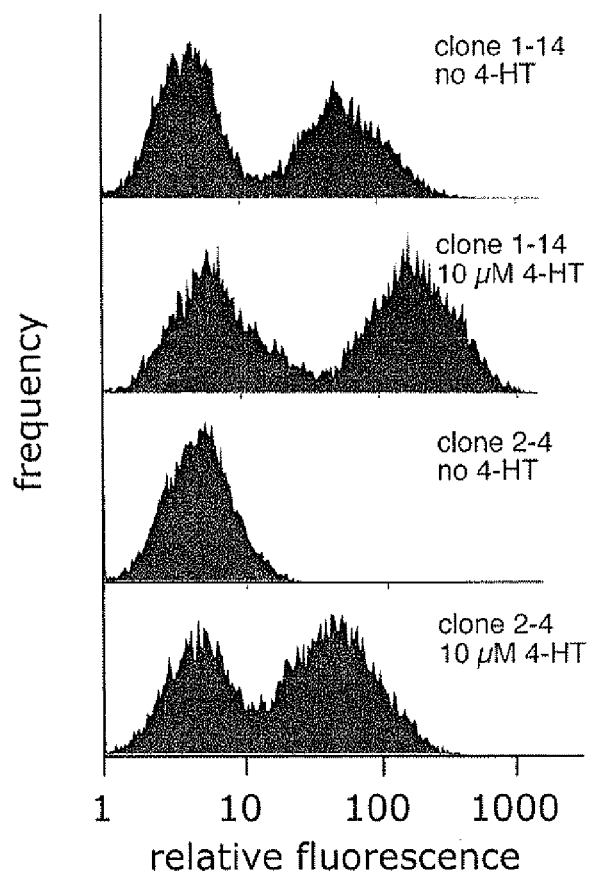
FIG. 2 shows the characterization of initial evolved inteins. (A) Yeast cultures expressing clones 1-14 and 2-4 inserted into GFP at position 108 were grown for 24 hours in the presence or absence of 10 µM 4-HT and analyzed by flow cytometry. The bimodal fluorescence distribution arises from loss of the GFP-encoding plasmid in the less fluorescent cells as revealed by their inability to grow on medium selective for the presence of the plasmid. (B) Protein splicing in clones 1-14, 2-4, and 2-5 was evaluated by Western blot analysis with an anti-GFP antibody after growth for 24 hours in the absence (−) or presence (+) of 10 µM 4-HT. Splicing removes the intein-ER fusion from the 74-kDa precursor (upper band) to yield the 27-kDa GFP (lower band).
Figure 2B:
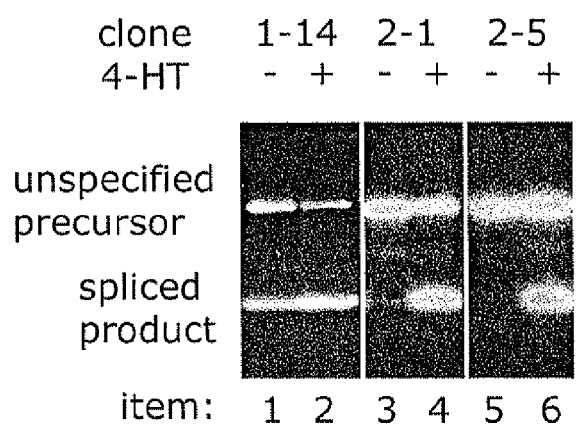

μM 4-HT was added, and aliquots were frozen rapidly at various time points to evaluate splicing kinetics by Western blot analysis (see FIG. 2B). (B) Yeast expressing intein 3-2-GFP were grown with varying concentrations of 4-HT for 28 hours and analyzed by flow cytometry to determine the dose dependence of intein activity. (C) Lanes: 1-4, yeast expressing intein 3-2-GFP were grown 20 hours in the absence or presence of 10 μM GDA and in the absence or presence of 10 μM 4-HT and then evaluated by Western blot; 5-7, in a separate experiment, yeast expressing intein 3-2-GFP were grown 16 hours to accumulate prespliced protein and then treated with 100 μg/ml cycloheximide for 1 hour followed by 10 μM GDA. Western blot analysis was performed on aliquots frozen 0, 2, and 6 hours after GDA treatment.

Figure 5:
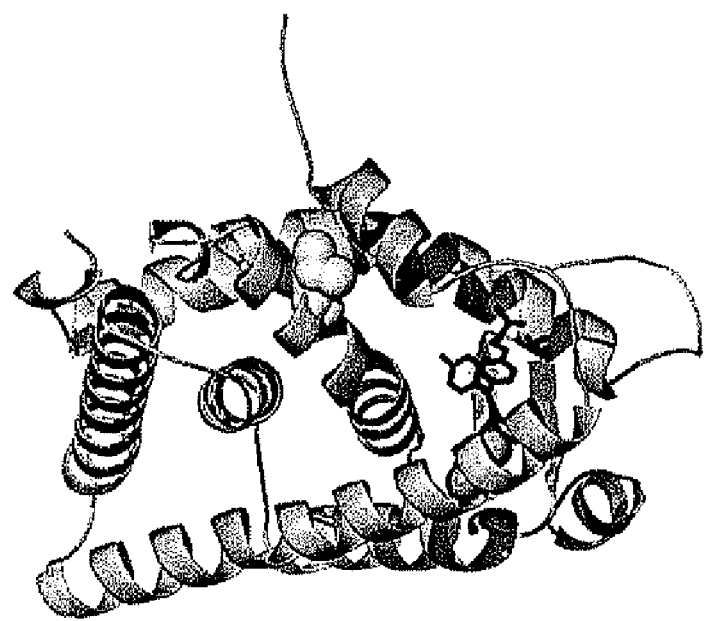
Figure 5:
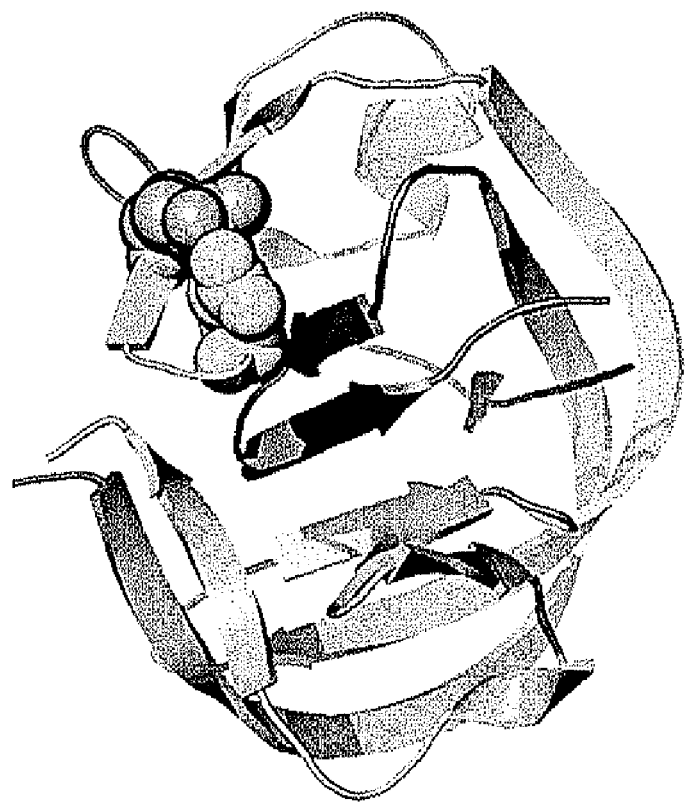
Figure 6A:
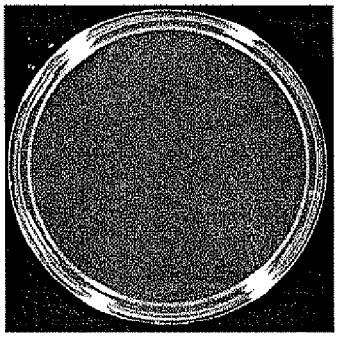
Figure 6A:
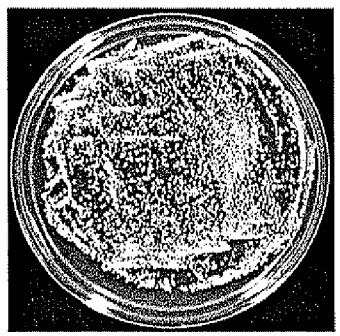
Figure 6B:
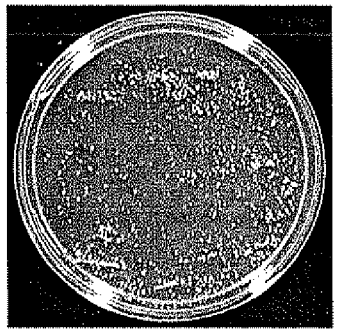
Figure 6B:
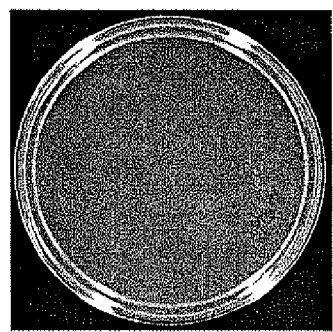

FIG. 5 shows mutations responsible for evolved ligand dependence. (Left) Intein mutations in the minimal 3-2 clone (Ala-34→Val, blue; and His-41→Leu, pink) are mapped onto the homologous Ssp DnaB mini-intein structure (Ding et al. *J. Biol. Chem.* 278:39133-39142, 2003; incorporated herein by reference). (Right) The location of acquired ER-LBD mutations of minimal clone 3-2 (Val-376→Ala, yellow; Arg-521→Gly, red) are mapped onto the ER-LBD structure, with helix 12 in orange and bound 4-HT in black (Shiau et al. *Cell* 95:927-37, 1998; incorporated herein by reference). Images were rendered with PYMOL.

FIG. 6 demonstrates intein-dependent geneticin resistance. (A) Yeast expressing KanR(N)-WT intein-KanR(C), but not yeast expressing KanR(N)-Cys-to-Ala mutant intein-KanR (C), in which the essential Cys after the intein is mutated to Ala, are able to grow in the presence of 150 μg/ml geneticin. (B) Yeast expressing KanR(N)-intein(N)-estrogen receptor ligand-binding domain (ER LBS)-intein (C)-KanR(C) are unable to grown in the presence of 150 μg/ml geneticin in the presence or absence of 4-hydroxytamoxifen (4-HT). The number of colony-forming units added to each plate is shown in the control plate lacking lacking geneticin (far right).

Figure 7:
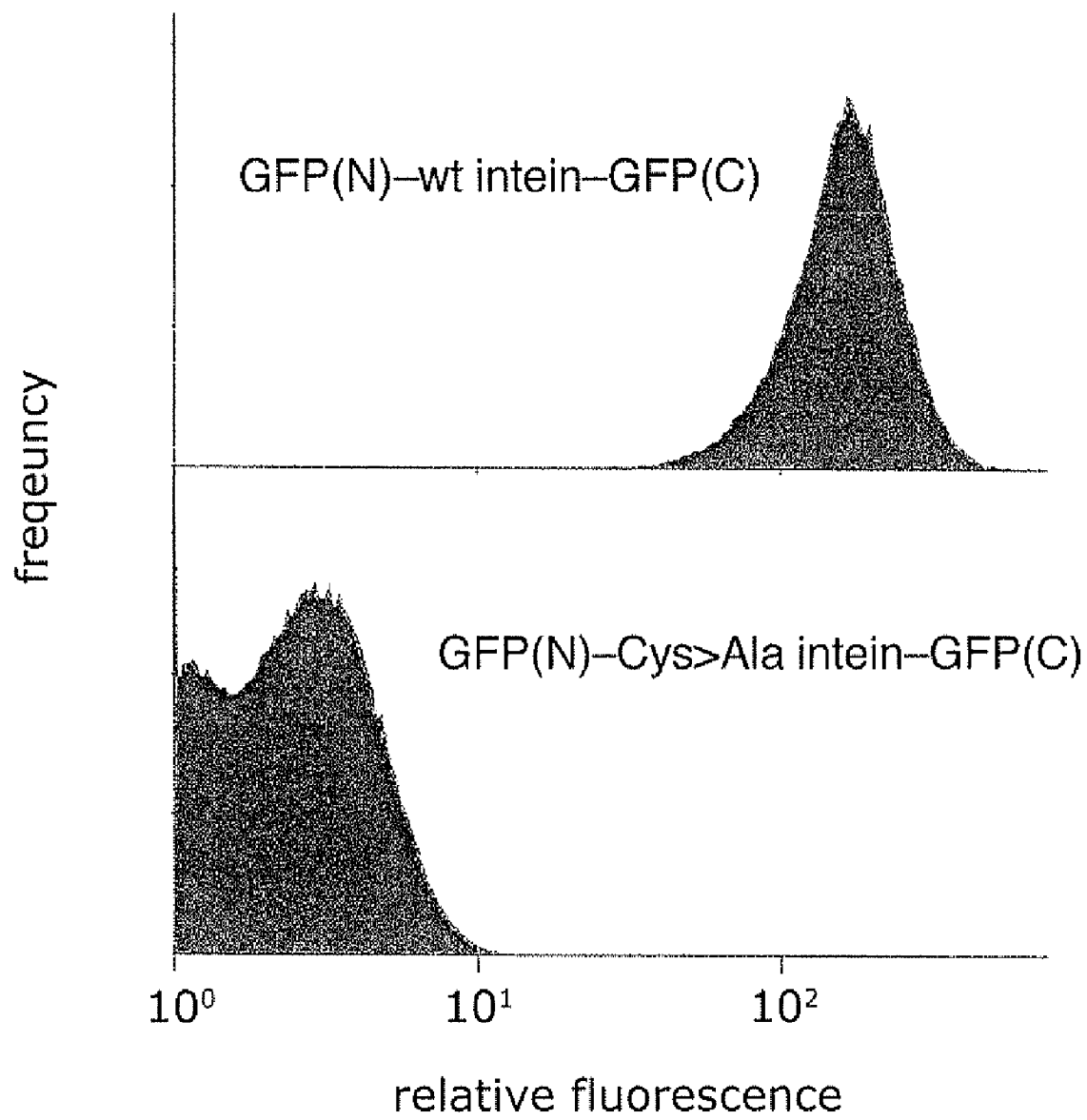

FIG. 7 demonstrates intein-dependent GFP fluorescence. Fluorescence-activated cell sorting (FACS) analysis of *Escherichia coli* expressing (GFP(N)-WT intein-GFP(C) or GFP(N)-Cys-to-Ala mutant intein-GFP(C), in which the essential Cys after the intein is mutated to Ala. Proteins were expressed by using arabinose-induced expression plasmid pBAD; cells were grown for 18 hours at 25° C. in medium containing 100 μg/ml ampicillin and 0.2% arabinose before FACS analysis.

FIG. 8 shows the properties of intein 2-4 in transiently transfected mammalian cells. (A) Cos-7 cells were transiently transfected with the ER-intein-GFP construct under the control of the pCIG promoter. 24 hours post-transfection, media containing 1 μM 4-HT was added. Cells were lysed at various time points after 4-HT addition for Western blot analysis. (B) Cos-7 cells were transiently transfected with the same ER-intein-GFP vector. 4 hours post-transfection, media containing 1 μM 4-HT was added. 21 hours after 4-HT addition, cells were analyzed by flow cytometry. For comparison, flow cytometric analysis was also performed on untransfected cells grown for the same amount of time, and on cells transfected at the same time but never exposed to 4-HT.

Figure 9:
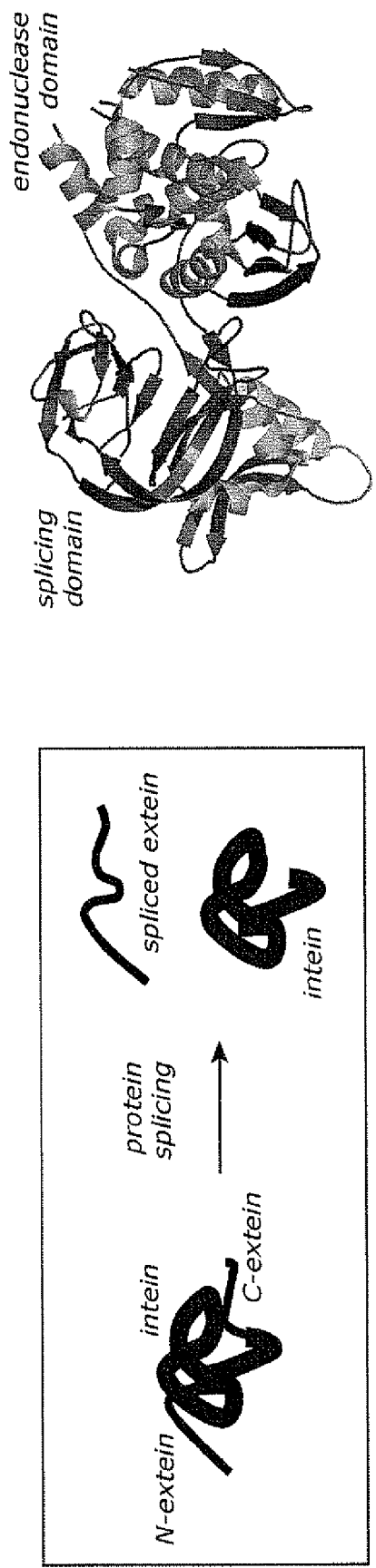

FIG. 9 illustrates inteins and their role in protein splicing. Disruption of proteins with inteins typically causes loss of function that is restored upon protein splicing. *M. tuberculosis* RecA intein splices in many extein contexts, but natural inteins are not switch-like. Questions to be answered include how can an intein acquire small molecule-dependence (Mootz et al., *J. Am. Chem. Soc.* 124:9044, 2002)?

Figure 10:
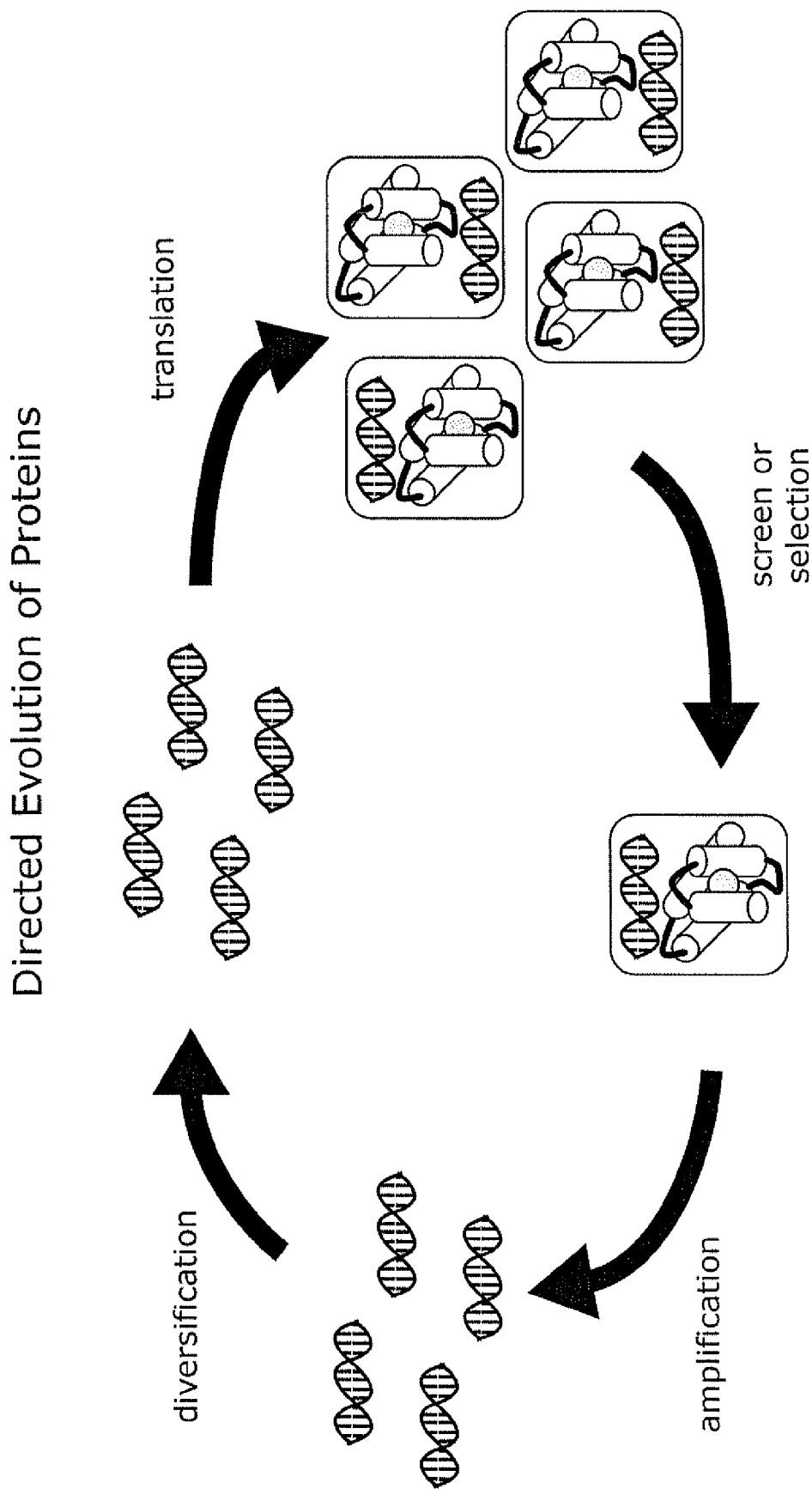

FIG. 10 shows how protein may be evolved through successive rounds of diversification, translation, screening or selection, and amplification.

Figure 11:
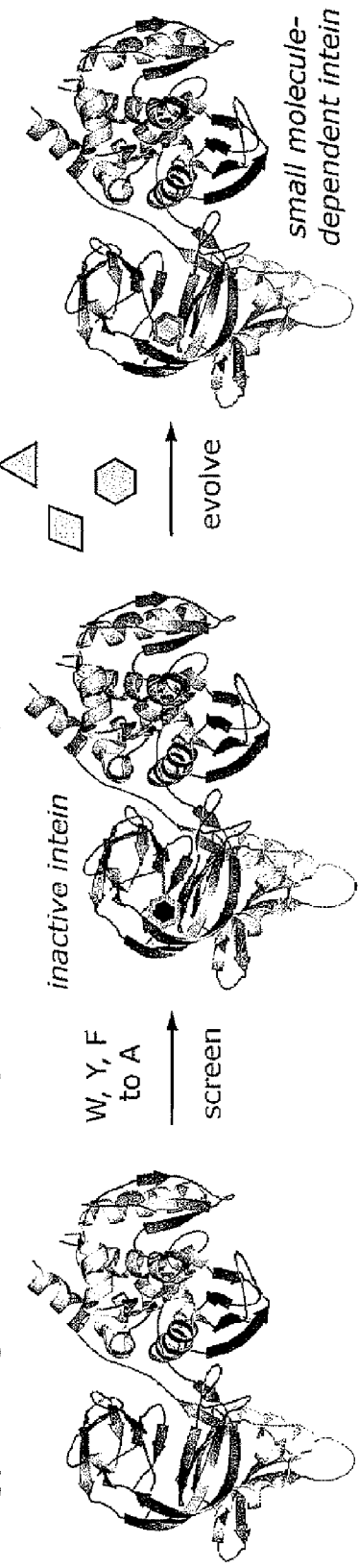
Figure 11:
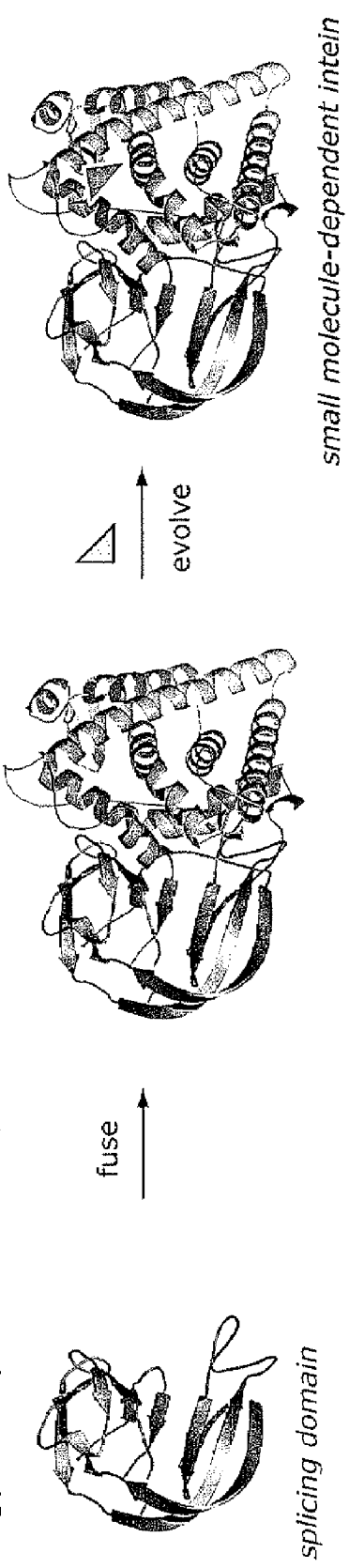

FIG. 11 illustrates a evolution-based approach for preparing ligand-dependent inteins. One strategy calls for engineering ligand binding sites in the intein followed by evolving ligand dependence. A second strategy involves using a ligand binding domain from a natural protein and then evolving ligand dependence.

Figure 12:
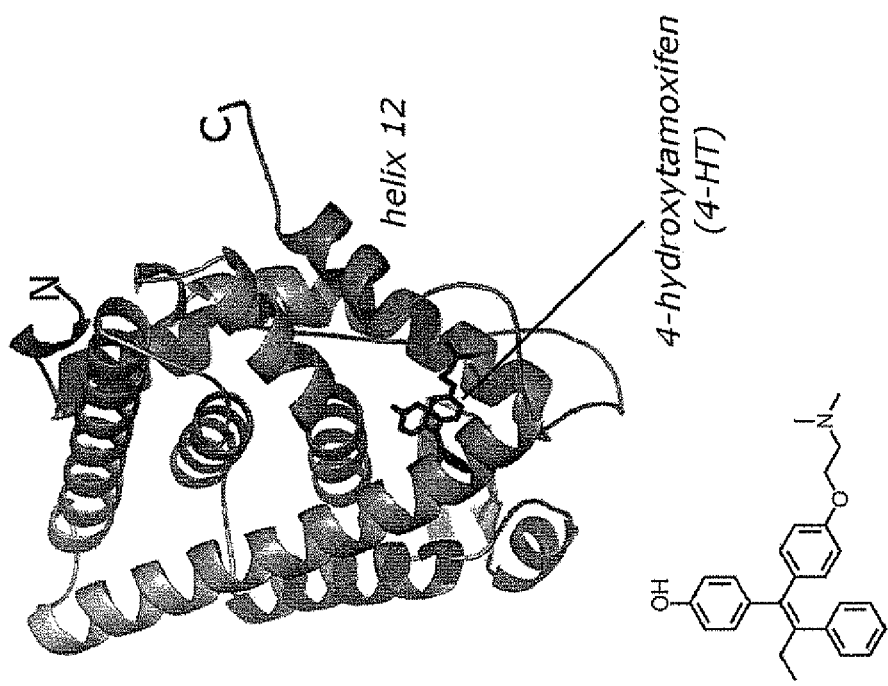

FIG. 12 shows a natural small molecule binding domain, the estrogen receptor (ER) ligand binding domain, which is known to bind 4-hydroxytamoxifen (4-HT). Binding of 4-HT to the ER ligand binding domain induces major conformational change of the ER and possible dissociation from Hsp90.

Figure 13:
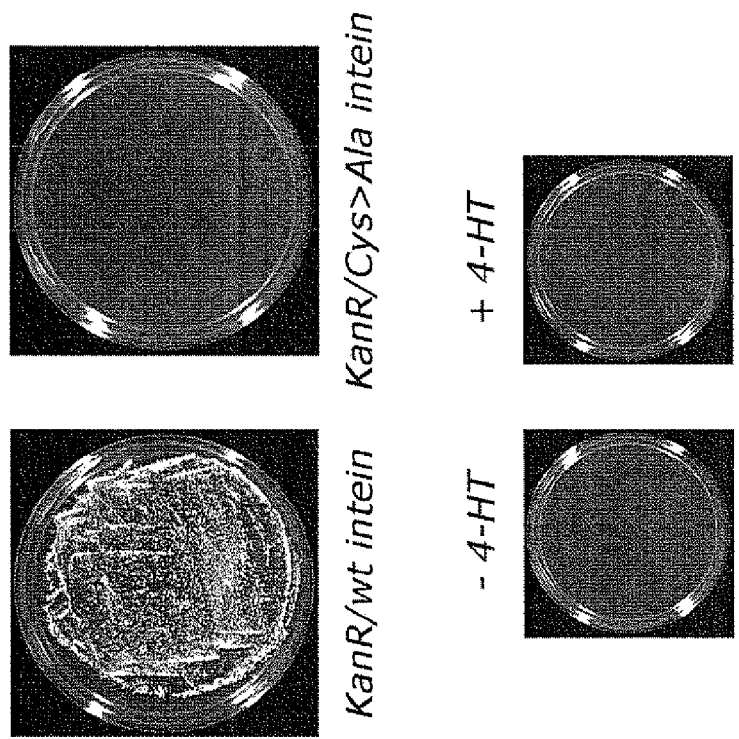
Figure 13:
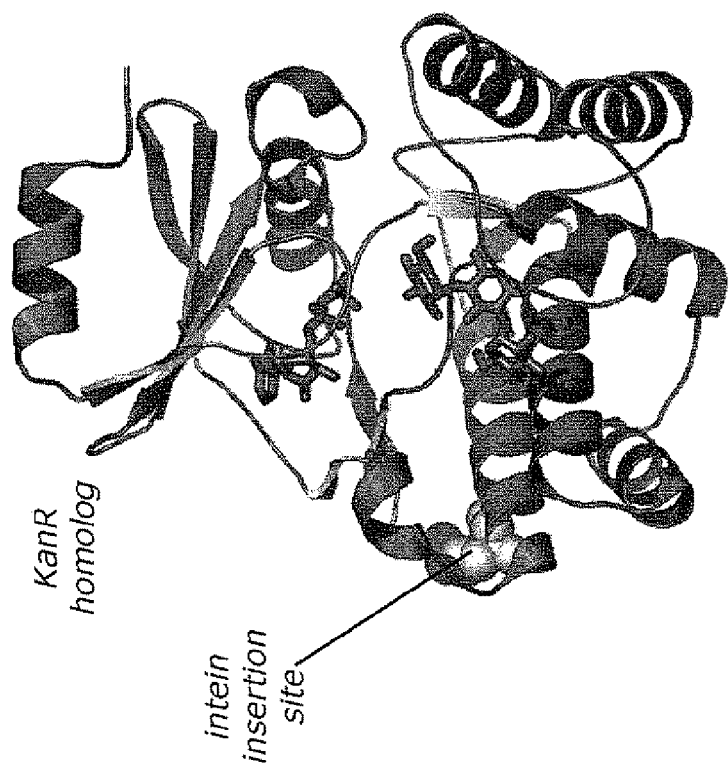

FIG. 13 shows the in vivo selections for intein activity using a geneticin resistance screen. Shown is the structure of the KanR homolog and the intein insertion site. KanR(N)-intein-KanR(C) confers geneticin resistance in yeast only if intein is active. Kan R(N)-intein(N)-ER-intein(C)-KanR(C) fails to confer geneticin resistance, and insertion of ER destroys intein activity.

Figure 14:
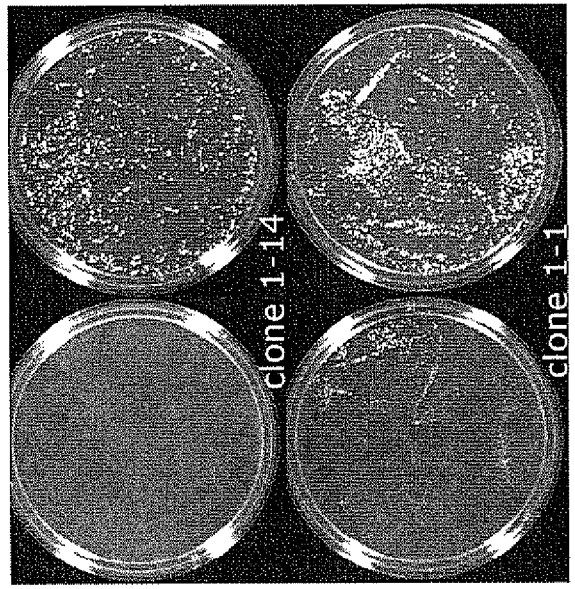

FIG. 14 shows round 1 selection yielding modest ligand-dependent splicing of the KanR(N)-intein(N)-ER-intein(C)-KanR(C) construct. The region that was diversified in round 1 selection is shown. Also shown are representative results from round 1 selection for clones 1-14 and 1-1. In round 1 selection, $6 \times 10^5$ point-mutated variants were tested and selected for correct splicing in the presence of 4-HT and geneticin. Increased geneticin resistance in the presence of 4-HT was observed for six clones.

Figure 15:
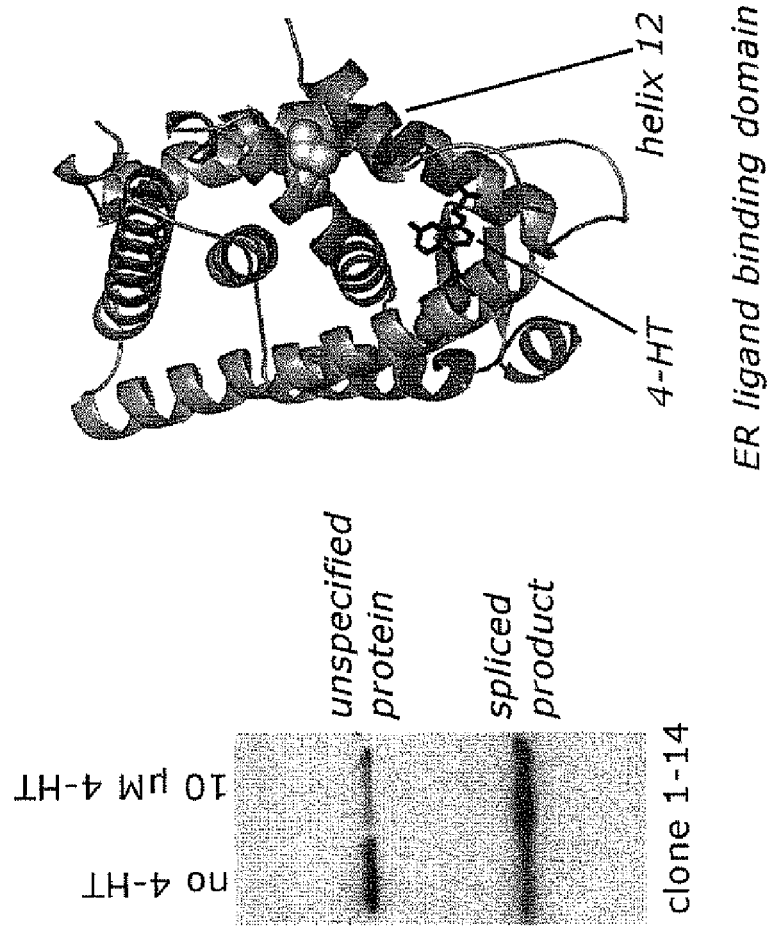

FIG. 15 illustrates the properties of round 1 ligand-dependent inteins. A western blot confirming modest ligand-dependent splicing relative to significant background is shown. Also shown is the ER ligand binding domain bound to 4-HT. Round 1 screening yielded three classes of mutations: (1) Val67Leu (intein) increases intein activity; (2) Tyr537His, Val376Ala (ER) disrupts helix 12 interactions with ER; and (3) Arg521Gly (ER) increases 4-HT affinity for ER 100-fold.

Figure 16:
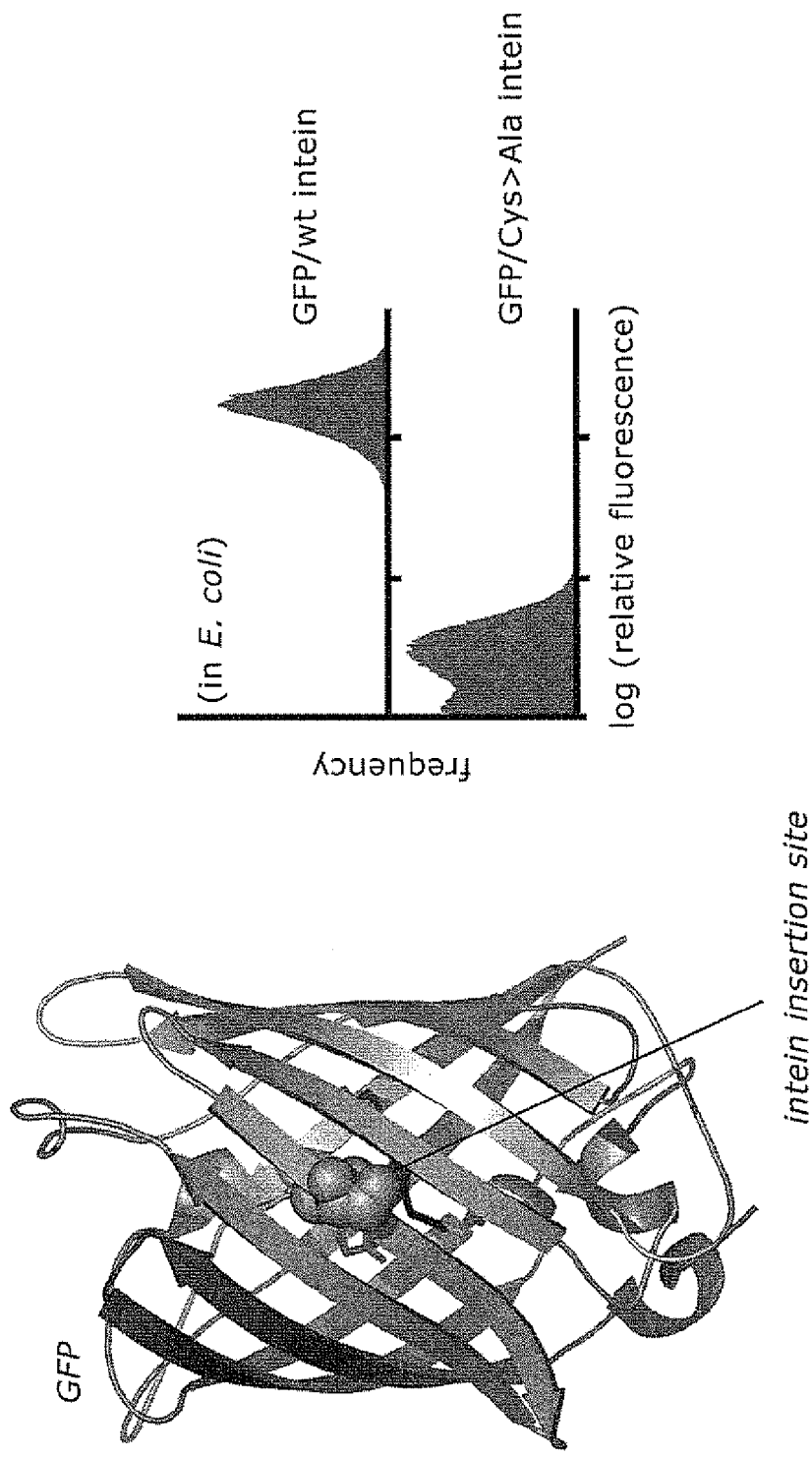

FIG. 16 shows a positive and negative in vivo screen for protein splicing based on green fluorescent protein (GFP), addressing the question of how to efficiently evolve the loss of splicing in the absence of 4-HT. Shown is the structure of GFP and its intein insertion site. The GFP(N)-intein-GFP(C) fluoresces only if intein is active. Shown is a representative fluorescence-activated cell sorting (FACS) analysis of GFP containing either a wild-type intein or a Cys→Ala mutated intein showing intein-dependent fluorescence. Note that both fluorescent and non-fluorescent cells can be isolated by FACS.

Figure 17:
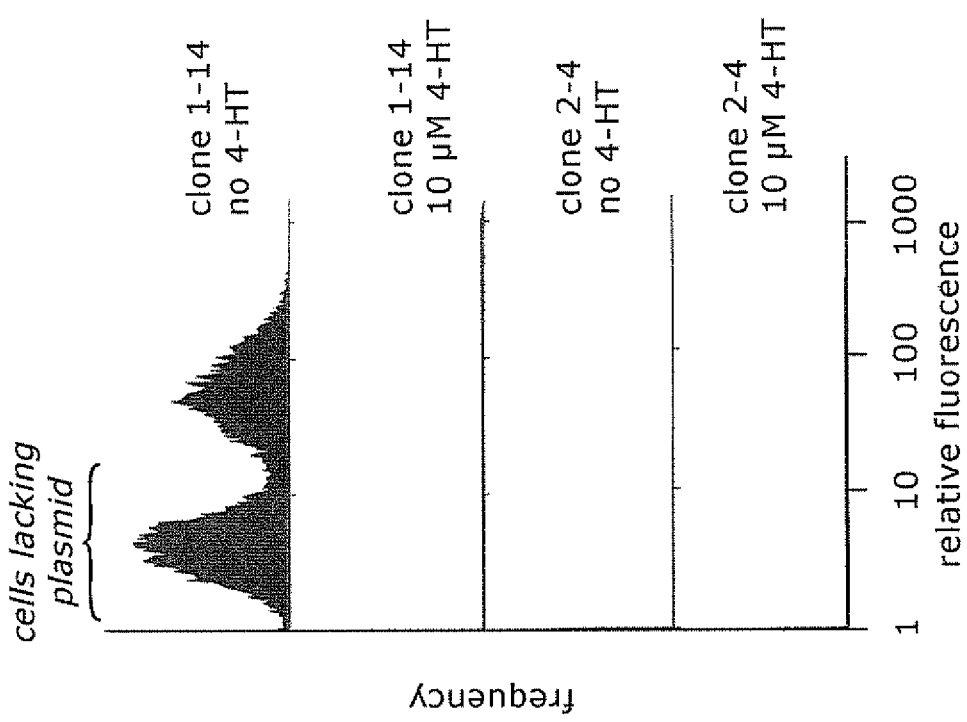

FIG. 17 shows FACS analysis of round 2 intein evolution using the GFP(N)-intein(N)-ER-intein(C)-GFP(C) construct. Point mutants of clones 1-1 and 1-14 were generated and $2 \times 10^6$ variants were identified and subjected to positive and negative screening that was conducted in the presence or absence, respectively, of 4-HT (5 screens total). Round 2 screening involves higher ligand dependence, but lower activity (meaning, no longer geneticin-resistant in the KanR context).

Figure 18:
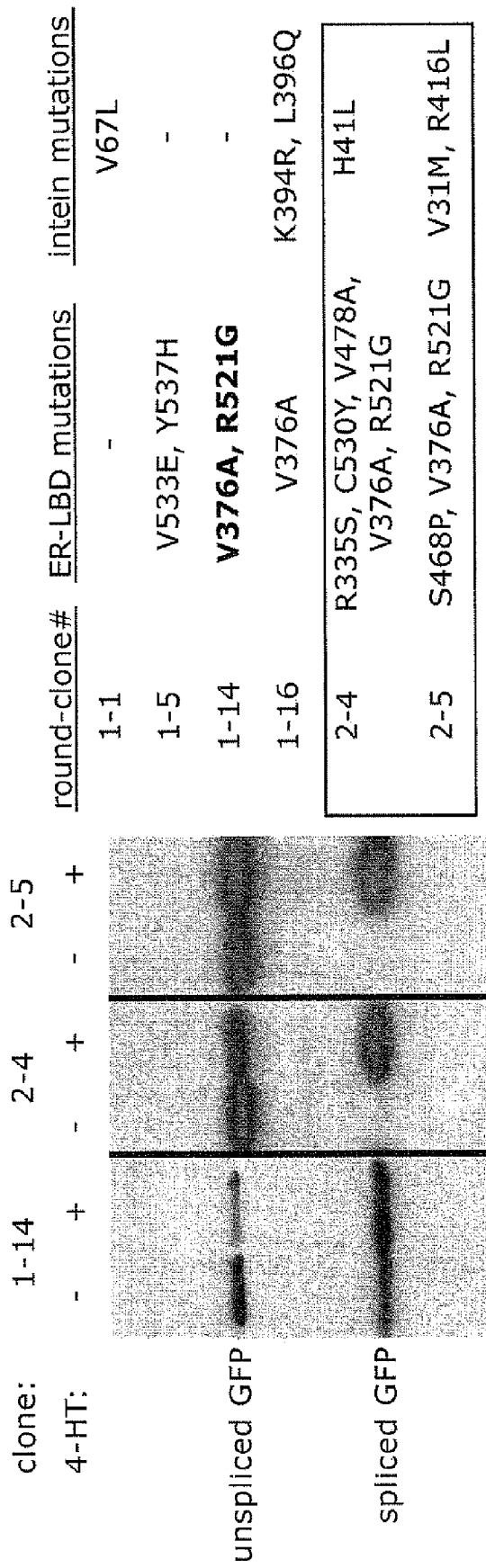

FIG. 18 shows the properties of round 2 evolved inteins. Protein splicing in clones 1-14, 2-4, and 2-5 was evaluated by western blot using an anti-GFP antibody after growth in the presence or absence of 4-HT. Shown in the chart are mutations within evolved inteins.

FIG. 19 shows round 3 intein evolution to yield high ligand dependence and more active inteins. Round 3 intein evolution involved generating point mutants and recombinants of round 2 clones ($2 \times 10^6$ variants). Positive selection was performed with 4-HT in the KanR context, and negative screening was performed in the absence of 4-HT in the GFP context. Clone 3-2 in the presence of 4-HT showed no background in GFP, but confers geneticin resistance in KanR.

Figure 20:
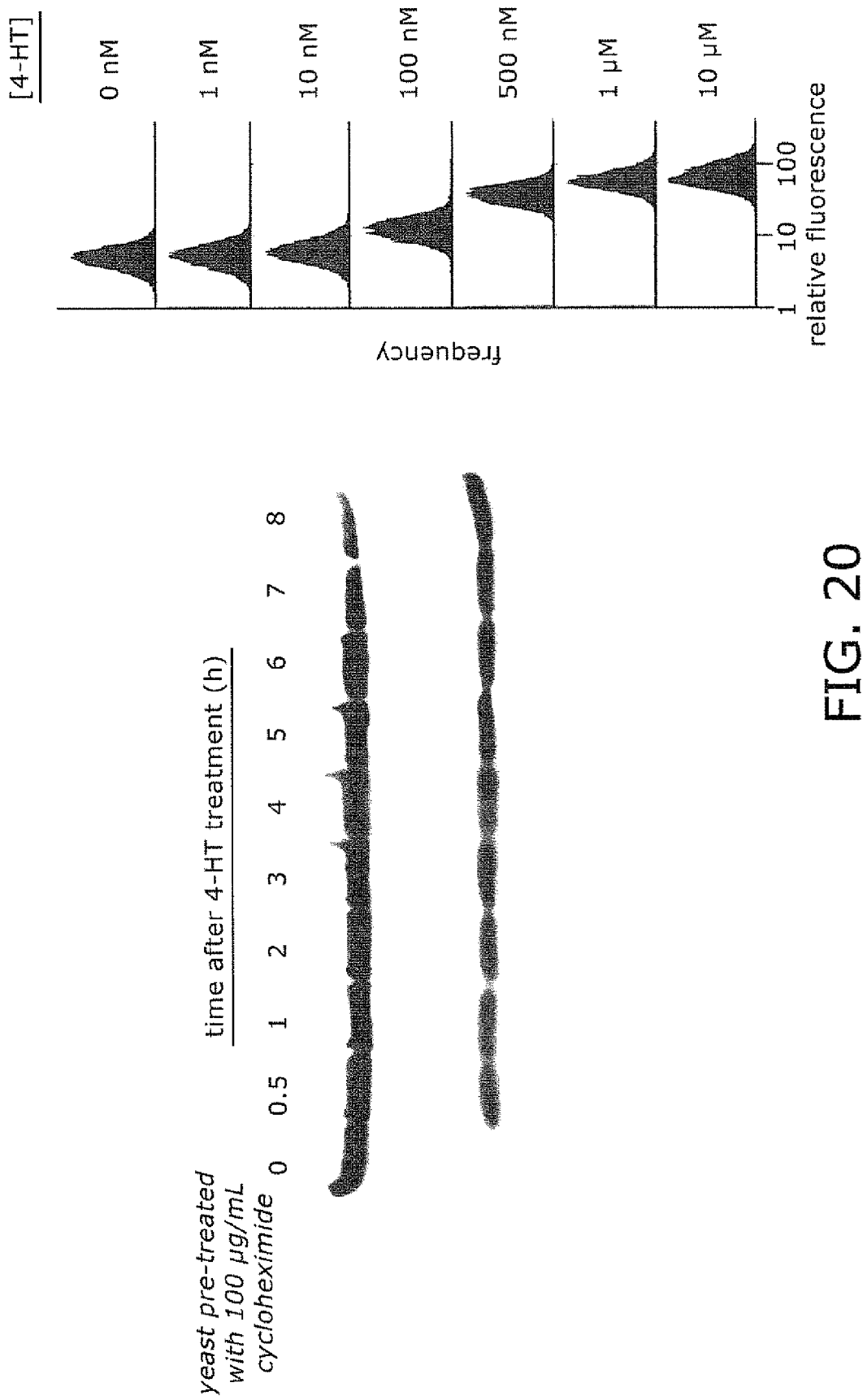

FIG. 20 shows the properties of round 3 evolved intein 3-2. Shown is a western blot of yeast pre-treated with 100 µg/ml cycloheximide. Splicing without 4-HT is not observed, showing that the intein acts as a post-translational switch. Splicing kinetics are fast (minutes to hours). FACS analysis shows that activation is 4-HT dose-dependent.

Figure 21:
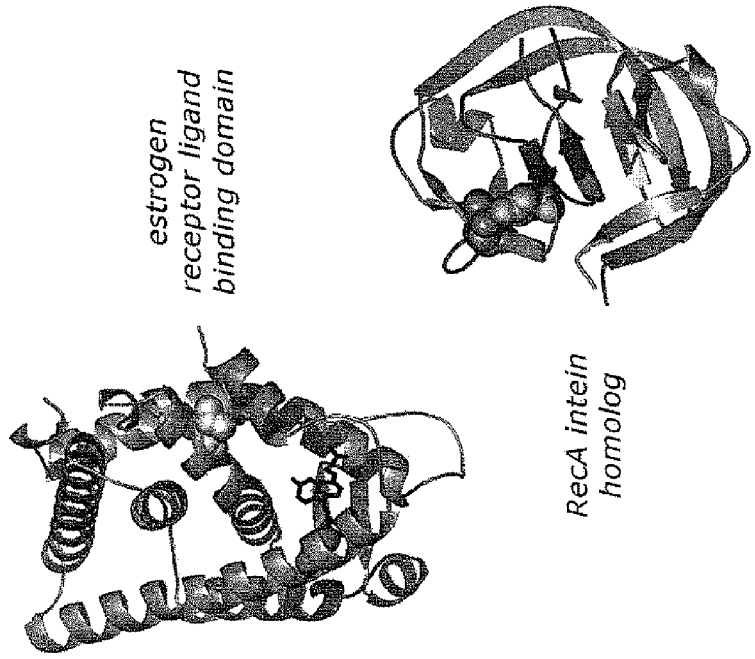

FIG. 21 shows the evolution ancestry of intein 3-2. The minimal 3-2 intein is phenotypically identical to evolved intein 3-2.

Figure 22:
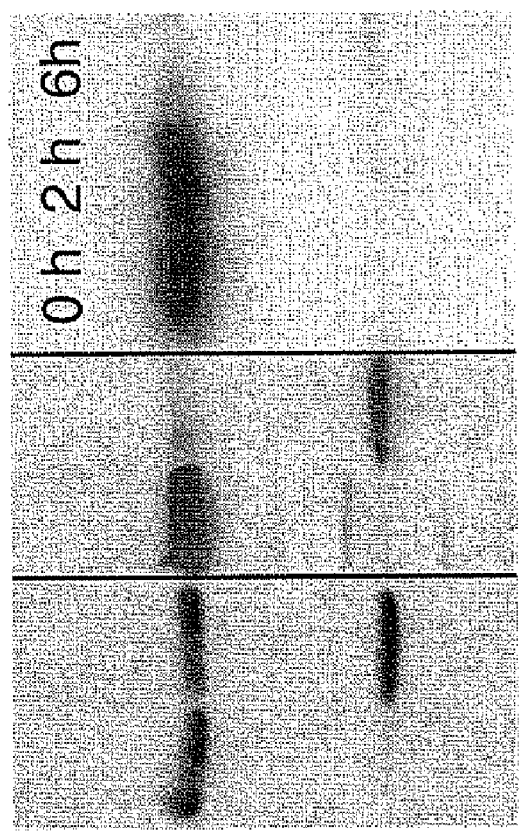

FIG. 22 tests two models for evolved ligand dependence. In the first model, Hsp90 complexes with ER and precludes intein folding. 4-HT works by dissociating Hsp90. In the second model, intein mutations destabilize folding, enabling ER to enforce non-splicing conformation. 4-HT induces conformational change tuned by ER mutations that restores splicing. In this experiment, geldanamycin (GDA, a small molecule inhibitor of Hsp90 function) treatment did not induce splicing of intein 3-2 in the absence of 4-HT, suggesting that Hsp90 activity is not required for inhibition of splicing.

Figure 23:
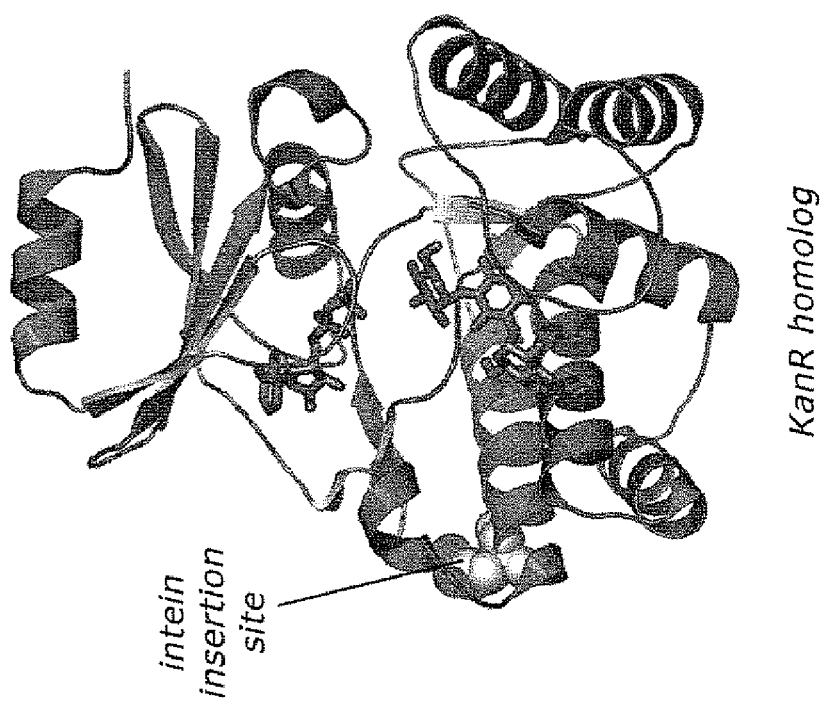
Figure 23:
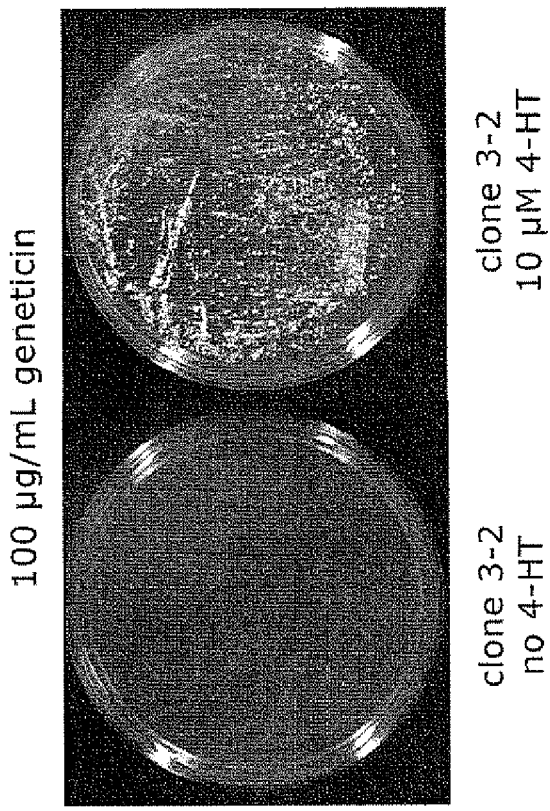

FIG. 23 shows the generality of an evolved protein switch. The evolved intein 3-2 is inserted into the helix/loop junction of KanR. Intein 3-2 is shown to be functional in the KanR context.

Figure 24:
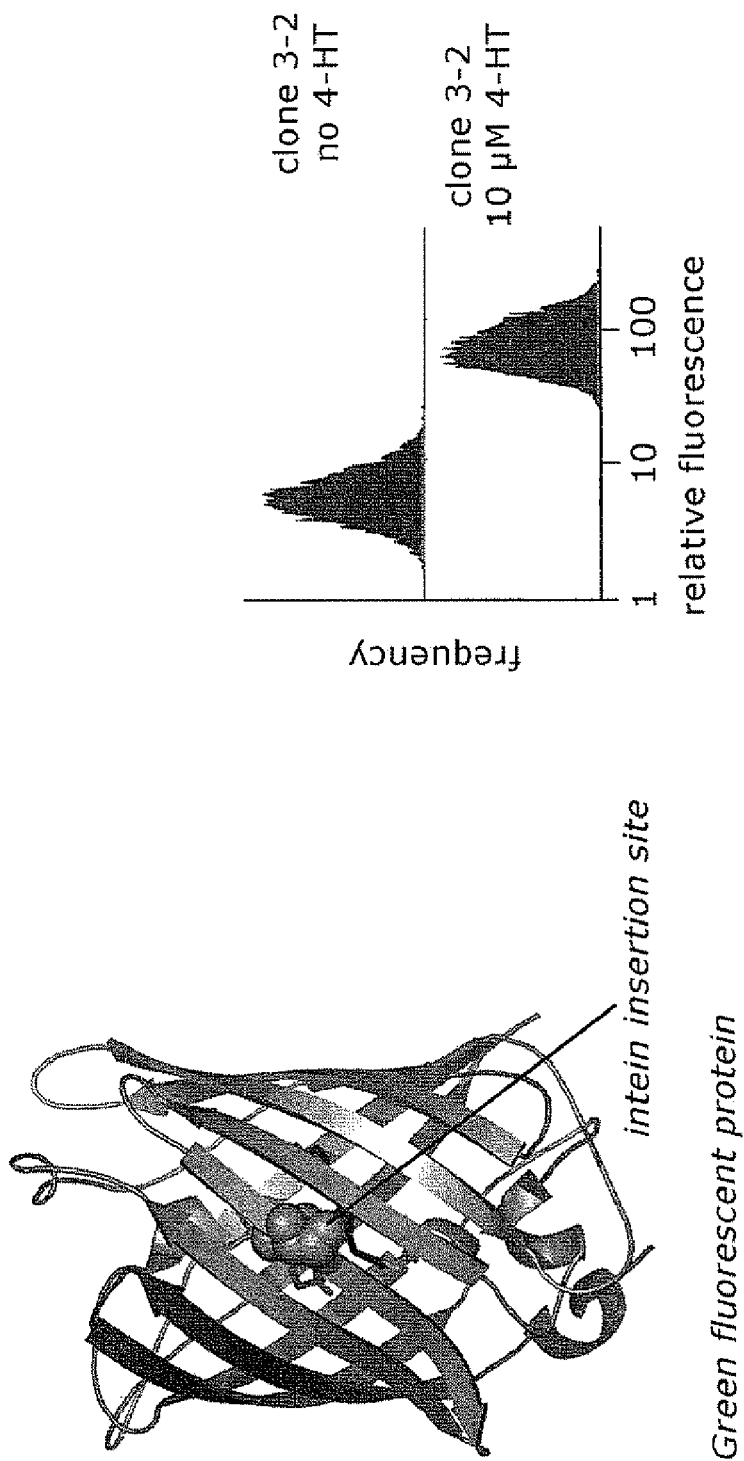

FIG. 24 shows the generality of an evolved protein switch. The evolved intein 3-2 is inserted into a β-strand of GFP. The intein 3-2 is shown to be functional in the GFP context.

Figure 25:
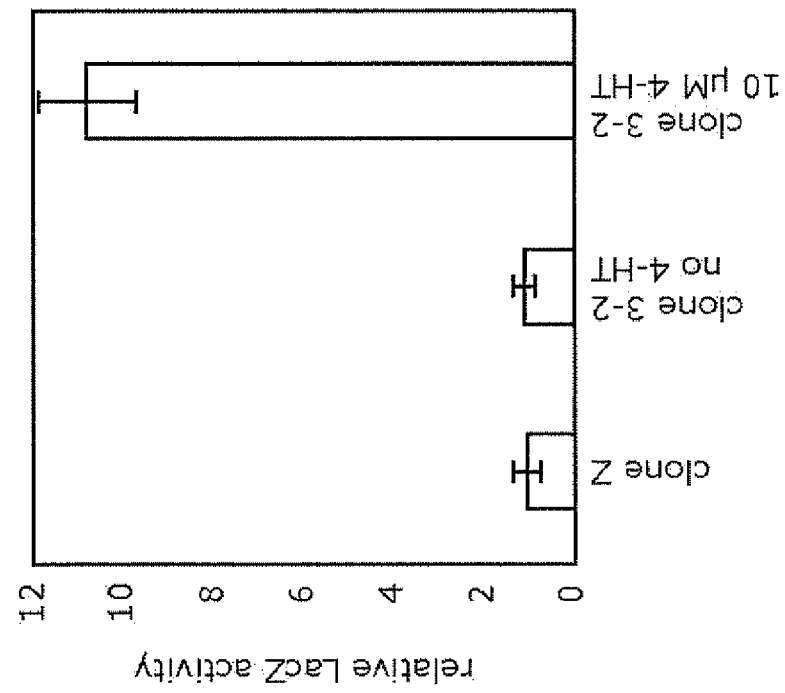
Figure 25:
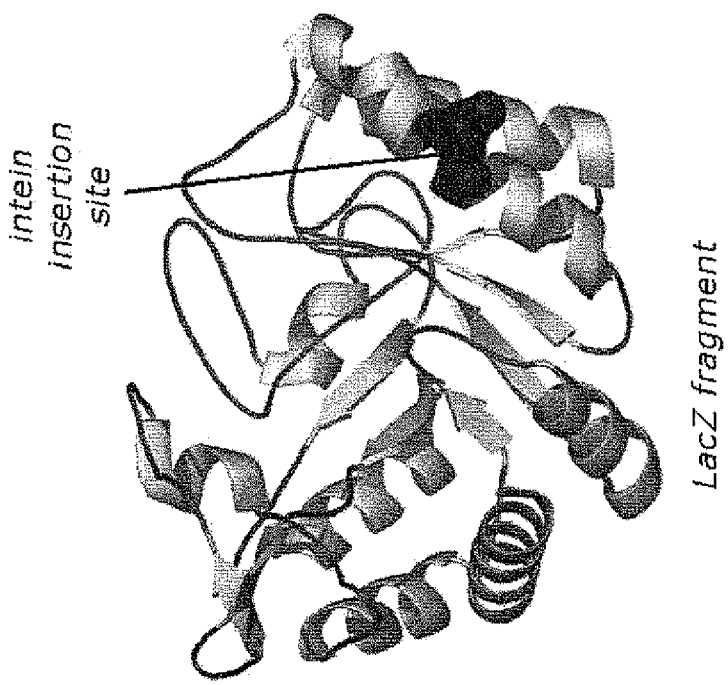

FIG. 25 shows the generality of an evolved protein switch. The evolved intein 3-2 is inserted into an α-helix of LacZ. The intein 3-2 is shown to be functional in the LacZ context.

Figure 26:
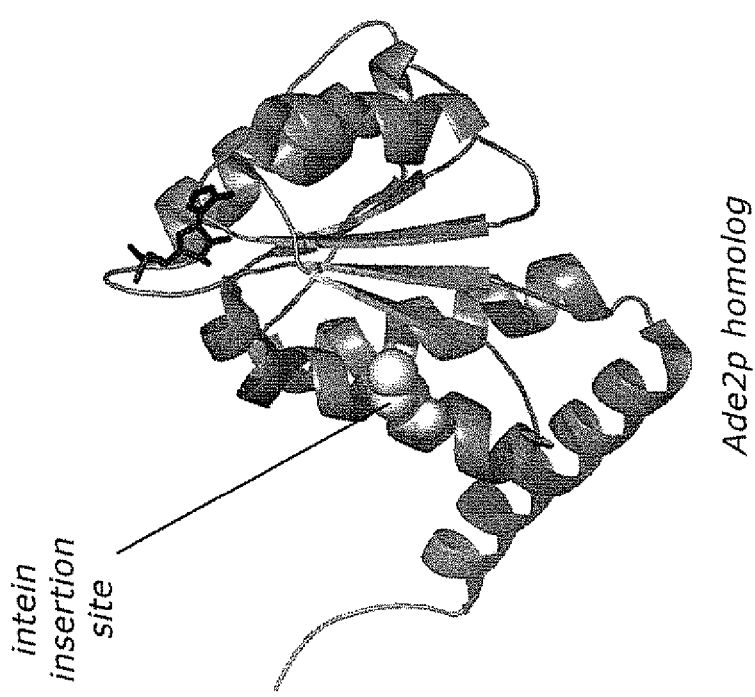
Figure 26:
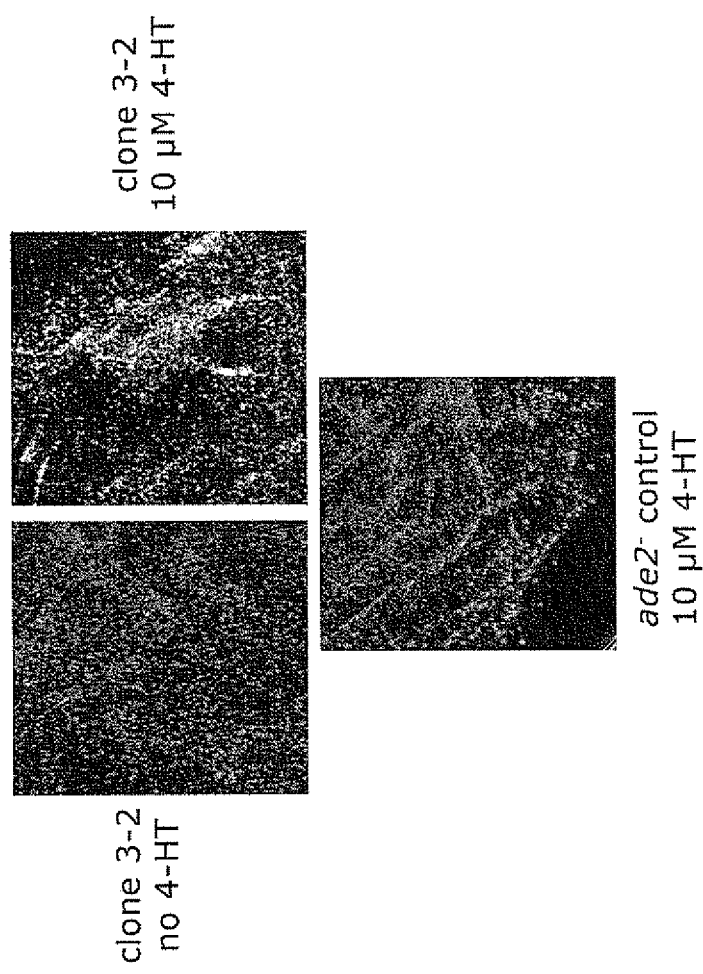

FIG. 26 shows the generality of an evolved protein switch. The evolved intein 3-2 is inserted into an α-helix of Ade2p. The intein 3-2 is shown to be functional in the Ade2p context.

DETAILED DESCRIPTION OF CERTAIN PREFERRED EMBODIMENTS OF THE INVENTION

The invention provides a system for preparing and/or using ligand-dependent inteins. Inteins are polypeptide sequences found in some proteins that catalyze their own excision from the peptide chain and ligation of the resulting ends. The reaction catalyzed by the intein results in a mature spliced protein and a free intein. Natural inteins spontaneously catalyze protein splicing. The invention provides ligand-dependent inteins. Ligand-dependent inteins are inteins whose splicing activity is dependent upon the binding of a ligand. In certain embodiments, the inventive ligand-dependent inteins are non-naturally occurring. By modulating the protein splicing activity of the intein, one is able to modulate the activity of a protein whose sequence has been modified by the insertion of a ligand-dependent intein sequence. The unspliced hybrid protein with the intein present has reduced or none of the biological activity of the mature spliced protein without the intein. Therefore, ligand-dependent inteins provide a way of modulating the activity of a protein by the addition of a ligand. Typically, one is able to modulate the activity of a protein faster using ligand-dependent inteins than using techniques for modulating transciption or translation since the inactive protein is already present in the cell and only needs to be spliced to become active. This technique allows for studying the role of a protein in a cell or biological pathway without having to discover a particular agent that modulates the activity of that particular protein because one ligand-dependent intein can be used in a variety of extein contexts.

Ligand-Dependent Intein

Ligand-dependent inteins, whose protein splicing activity depends on the presence of a particular ligand, are engineered or evolved starting from a known intein sequence. The known intein sequence is modified to add a ligand binding domain, and the resulting construct is evolved to produce a ligand-dependent intein.

Any protein sequence that catalyzes its own excision from a polypeptide sequence is an intein which can be utilized. Many natural intein sequences are known in the art and may be used to develop ligand-dependent inteins. A database of known intein sequences is InBase (Perler, F. B. (2002). InBase, the Intein *Database. Nucleic Acids Res.* 30:383-384; incorporated herein by reference). Any of the intein sequences listed in this database or subsequently discovered may be used as starting points in the development of ligand-dependent inteins. The intein may be derived from a prokaryotic source or a eukaryotic source. The intein may be derived from a bacterial source, an archaebacterial source, a yeast source, a mammalian source, a human source, etc. In the Examples below, the RecA intein from *M. tuberculosis* was used to develop a 4-hydroxytamoxifen-dependent intein. Other non-limiting examples of inteins which may be used include *Thermococcus litoralis* DNA polymerase (Tli pol intein-1 and Tli pol intein-2), Psp IVPS 1, *Pyrococcus* polymerase intein (Psp pol intein), and the *Saccharomyces cerevisiae* TFP1 (Sce VMA intein). As well as naturally occurring inteins, unnatural intein sequences may also be used to create ligand-dependent inteins. In certain embodiments, the intein may be a modified or mutated version of a naturally occurring intein. In certain embodiments, the intein is a well characterized intein. For example, the structure of the intein may be known. Preferably, the intein sequence chosen as the starting point for designing a ligand-dependent intein should be amenable to manipulation and catalyze protein splicing in a variety of extein contexts. In certain embodiments, inteins that require particular amino acid sequences in the flanking exteins are avoided.

Preferably, when the intein excises itself from the protein and ligates the resulting ends together no "scar" or a minimal "scar" is left. The splicing reaction either leaves no amino acids from the intein sequence or just a short sequence of one, two, or three amino acids. In certain preferred embodiments, the intein leaves no amino acids in the mature protein. In other embodiments, the intein may leave one amino acid such as a cysteine. If the intein does leave a "scar" in the mature protein, the "scar" should not, or at least minimally, interfere with the activity of the mature protein.

Once the sequence of the intein to be used has been determined, the corresponding polynucleotide encoding that amino acid sequence is prepared. The polynucleotide sequence can be prepared using any techniques known in the art for recombinant DNA technology (please see, *Molecular Cloning: A Laboratory Manual,* 2nd Ed., ed. by Sambrook, Fritsch, and Maniatis (Cold Spring Harbor Laboratory Press: 1989); *Nucleic Acid Hybridization* (B. D. Hames & S. J. Higgins eds. 1984); the treatise, *Methods in Enzymology* (Academic Press, Inc., N.Y.); *Immunochemical Methods in Cell and Molecular Biology* (Mayer and Walker, eds., Academic Press, London, 1987); Ausubel et al. *Current Protocols in Molecular Biology* (John Wiley & Sons, Inc., New York, 1999); *Transcription and Translation* (B. D. Hames & S. J. Higgins eds. 1984); *Handbook of Experimental Immunology,* Volumes I-IV (D. M. Weir and C. C. Blackwell, eds., 1986);

each of which is incorporated herein by reference). In certain embodiments, the polynucleotide is synthesized using a DNA synthesizer. In other embodiments, the polynucleotide may be excised from a vector or other polynucleotide with the sequence (e.g., using restriction enzymes). In yet other embodiments, the polymerase chain reaction may be used to isolate and amplify the desired sequence. The polynucleotide may be prepared so that the sequence contains restriction sites for easily manipulating the polynucleotide sequence (e.g., subcloning the sequence into a vector or inserting the sequence into a target protein). The polynucleotide may also be prepared with a mutation in the sequence. In certain embodiments, the codon usage may be optimized for expression in a particular organism such as E. coli, S. cerevisiae, mouse, rat, human, etc.

In addition to the intein, a ligand binding domain must also be chosen to insert into the intein. The ligand binding domain may be any natural or unnatural protein domain that binds a ligand. Preferably, the domain binds the ligand with specificity. Also, preferably the domain binds the ligand with high affinity. In certain embodiments, the domain binds its ligand at at least $10^{-9}$ M, $10^{-8}$ M, $10^{-7}$ M, $10^{-6}$, $10^{-5}$, $10^{-4}$ M, or $10^{-3}$ M. The domain should be a self-contained unit which can properly fold and binds its ligand in a variety of intein contexts. The ligand may be any chemical compound such as a small molecule, a peptide, a protein, a polynucleotide, a nucleotide, a nucleoside, an amino acid, a lipid, a carbohydrate, a natural product, a metabolite, a metal, an organometallic complex, a drug, or a biomolecule. In certain embodiments, the ligand is a small molecule. In other embodiments, the ligand is a peptide. The ligand binding domain may range from 50 to 400 amino acids, preferably 100-300 amino acids. Examples of ligand binding domains useful in the invention include the ligand binding domains of known small molecule receptor (e.g., the ligand binding domain of the estrogen receptor), the antigen binding region of an antibody, allosteric binding sites of proteins, substrate binding sites of enzymes, etc. The polynucleotide encoding the ligand binding domain is prepared using any techniques known in the art including those described above for preparing the polynucleotide encoding the intein.

Ideally, binding of the ligand to the ligand binding domain should cause the intein to regain its protein splicing activity. In certain embodiments, a conformational change in the ligand binding domain upon ligand binding causes the intein to regain its protein splicing activity. For example, binding of the ligand may cause the N- and C-termini of the ligand binding domain to move into closer proximity, thereby restoring the protein splicing activity of the intein. In certain embodiments, the protein splicing activity of the intein-ligand binding domain construct may not be initially modulated by ligand binding. The construct may need to be engineered or evolved to gain or to optimize this activity. However, in choosing the ligand binding domain the conformational changes induced in the domain upon ligand binding should be considered.

After the intein sequence and ligand binding domain have been chosen, the polynucleotide sequence encoding the ligand binding domain is inserted into the polynucleotide sequence encoding the intein sequence. The ligand binding domain may be inserted anywhere in the intein sequence. The domain is preferably inserted into the intein such that the splicing activity of the intein is minimal or non-existent. The domain is inserted in frame into the intein sequence. The insertion may be performed using any techniques known in the art. In certain embodiments, the domain is inserted into the intein polynucleotide by cutting out the polynucleotide encoding the domain using restriction enzymes and ligating this fragment into a cut vector containing the polynucleotide sequence. This provides the starting intein-ligand binding domain construct for screening, evolution, or other manipulation. Typically, the construct will have the structure:

Intein (N)-Ligand Binding Domain-Intein(C)

wherein the ligand binding domain is situated in between an N-terminal portion of the intein sequence and a C-terminal portion of the intein. The ligand binding domain may also be placed at either of the two termini of the intein sequence.

In certain embodiments, the ligand-dependent intein is derived from the following sequence which is the original RecA intein sequence with the estrogen receptor ligand binding domain inserted in place of the RecA endonuclease domain with six-amino-acid linkers in between:

```
                                            (SEQ ID NO: 1)
CLAEGTRIFDPVTGTTHRIEDVVDGRKPIHVVAAAKDGTLHARPVVSWFD

QGTRDVIGLRIAGGAIVWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQVHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNKRMEHLYSMKCKNVVPLYDLLLEMLDAHRLHAGG

SGASRVQAFADALDDKFLHDMLAEELRYSVIREVLPTRRARTFDLEVEEL

HTLVAEGVVVHN.
```

The starting sequence was constructed as follows:

residues 1-94 of the RecA intein:

```
                                            (SEQ ID NO: 2)
[1 (1) - CLAEGTRIFDPVTGTTHRIEDVVDGRKPIHVVAAAKDGTLH

ARPVVSWFDQGTRDVIGLRIAGGAIVWATPDHKVLTEYGWRAAGELRKGD

RVA - 94 (94)];
``` a six amino acid linker:

```
    [(95) - GPGGSG - (100)];        (SEQ ID NO: 3)
``` residues 304-551 of the human estrogen receptor, comprising the ligand binding domain:

```
                                            (SEQ ID NO: 4)
[304 (101) - NSLALSLTADQMVSALLDAEPPILYSEYDPTRPFSEA

SMMGLLTNLADRELVHMINWAKRVPGFVDLTLHDQVHLLECAWLEILMIG

LVWRSMEHPGKLLFAPNLLLDRNQGKCVEGMVEIFDMLLATSSRFRMMNL

QGEEFVCLKSIILLNSGVYTFLSSTLKSLEEKDHIHRVLDKITDTLIHLM

AKAGLTLQQQHQRLAQLLLILSHIRHMSNKRMEHLYSMKCKNVVPLYDLL

LEMLDAHRLHA - 551 (348)];
``` a six amino acid linker:

[(349)-GGSGAS-(354) (SEQ ID NO: 5)]; and residues 383-440 of the RecA intein:

(SEQ ID NO: 6)
[383 (355) - RVQAFADALDDKFLHDMLAEELRYSVIREVLPTRRAR

TFDLEVEELHTLVAEGVVVHN - 440 (412)]].

The numbering of the amino acid residues of the parental sequence are shown in bold. The number of the amino acid residues of the construct as a whole are shown in parentheses. That is, residue 1 of the RecA intein corresponds to residue 1 of the construct as a whole. Residue 304 of the estrogen receptor ligand binding domain corresponds to residue 101 of the construct as a whole, and residue 383 of the RecA intein corresponds to residue 355 of the construct as a whole.

The sequence of the ligand-dependent intein may have 1, 2, 3, 4, 5, 6, 7, 8, 9, or 10 point mutations as compared to the starting sequence. In certain embodiments, the ligand-dependent intein is 85%, 90%, 95%, 96%, 97%, 98%, or 99% homologous to the starting sequence. In certain particular embodiments, the ligand-dependent intein has the sequence:

1-1:
(SEQ ID NO: 7)
CLAEGTRIFDPVTGTTHRIEDVVDGRKPIHVVAAAKDGTLHARPVVSWFD

QGTRDVIGLRIAGGAILWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQVHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNKRMEHLYSMKCKNVVPLYDLLLEMLDAHRLHAGG

SGASRVQAFADALDDKFLHDMLAEELRYSVIREVLPTRRARTFDLEVEEL

HTLVAEGVVVHN;

1-5:
(SEQ ID NO: 8)
CLAEGTRIFDPVTGTTHRIEDVVDGRKPIHVVAAAKDGTLHARPVVSWFD

QGTRDVIGLRIAGGAIVWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQVHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNKRMEHLYSMKCKNEVPLHDLLLEMLDAHRLHAGG

SGASRVQAFADALDDKFLHDMLAEELRYSVIREVLPTRRARTFDLEVEEL

HTLVAEGVVVHN;

1-14:
(SEQ ID NO: 9)
CLAEGTRIFDPVTGTTHRIEDVVDGRKPIHVVAAAKDGTLHARPVVSWFD

QGTRDVIGLRIAGGAIVWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQAHLLECAWLEILMIGLVWRSMEHPGKLL

-continued

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNKGMEHLYSMKCKNVVPLYDLLLEMLDAHRLHAGG

SGASRVQAFADALDDKFLHDMLAEELRYSVIREVLPTRRARTFDLEVEEL

HTLVAEGVVVHN 1-16:
(SEQ ID NO: 10)
CLAEGTRIFDPVTGTTHRIEDVVDGRKPIHVVAAAKDGTLHARPVVSWFD

QGTRDVIGLRIAGGAIVWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNKRMEHLYSMKCKNVVPLYDLLLEMLDAHRLHAGG

SGASRVQAFADALDDRFQHDMLAEELRYSVIREVLPTRRARTFDLEVEEL

HTLVAEGVVVHN;

2-4:
(SEQ ID NO: 11)
CLAEGTRIFDPVTGTTHRIEDVVDGRKPIHVVAAAKDGTLLARPVVSWFD

QGTRDVIGLRIAGGAIVWATPDHKVLTEYGWRAAGELRKGDRVAGPGGSG

NSLALSLTADQMVSALLDAEPPILYSEYDPTSPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGG

SGASRVQAFADALDDKFLHDMLAEELRYSVIREVLPTRRARTFDLEVEEL

HTLVAEGVVVHN;

2-5:
(SEQ ID NO: 12)
CLAEGTRIFDPVTGTTHRIEDVVDGRKPIHMVAAAKDGTLHARPVVSWFD

QGTRDVIGLRIAGGAIVWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKPLEEKDHIHRVLDKITDTLIHLMAKAGLTLQQQHQR

LAQLLLILSHIRHMSNKGMEHLYSMKCKNVVPLYDLLLEMLDAHRLHAGG

SGASRVQAFADALDDKFLHDMLAEERYSVIREVLPTLRARTFDLEVEELH

TLVAEGVVVHN;

3-2:
(SEQ ID NO: 13)
CLAEGTRIFDPVTGTTHRIEDVVDGRKPIHVVAVAKDGTLLARPVVSWFD

QGTRDVIGLRIAGGAIVWATPDHKVLTEYGWRAAGELRKGDRVAGPGGSG

NSLALSLTADQMVSALLDAEPPILYSEYDPTSPFSEASMMGLLTNLADRE

LVHMINWAKRVPGFVDLTLHDQAHLLECAWLEILMIGLVWRSMEHPGKLL

-continued

FAPNLLLDRNQGKCVEGMVEIFDMLLATSSRFRMMNLQGEEFVCLKSIILL

NSGVYTFLSSTLKSLEEKDHIHR<u>A</u>LDKITDTLIHLMAKAGLTLQQQHQRLA

QLLLILSHIRHMSNK<u>G</u>MEHLYSMK<u>YT</u>NVVPLYDLLLEMLDAHRLHAGGSGA

SRVQAFADALDDKFLHDMLAEELRYSVIREVLPTRRARTFDLEVEELHTLV

AEGVVVHN;
or

Min. 3-2:

(SEQ ID NO: 14)
CLAEGTRIFDPVTGTTHRIEDVVDGRKPIHVVA<u>V</u>AKDGTL<u>L</u>ARPVVSWFD

QGTRDVIGLRIAGGAIVWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQ<u>A</u>HLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNK<u>G</u>MEHLYSMKCKNVVPLYDLLLEMLDAHRLHAGG

SGASRVQAFADALDDKFLHDMLAEELRYSVIREVLPTRRARTFDLEVEEL

HTLVAEGVVVHN.

The underlined amino acids indicate mutations from the original starting sequence. In certain embodiments, the 3-2 or minimal 3-2 sequence is preferred. In certain embodiments, the intein exhibits minimal background splicing in the absence of ligand and an increase of 2-fold, 5-fold, 10-fold, 100-fold, or 1000-fold splicing activity in the presence of ligand.

Target Protein

Once the intein-ligand binding domain construct is prepared, the construct is inserted into a target protein, thereby allowing for modulation of the protein's activity based on the presence or absence of the ligand. The insertion of the ligand-dependent intein into a target protein creates a hybrid protein. Any protein can be a target protein. In certain embodiments, the protein is one whose activity in the cell or in a biochemical pathway is being studied. In other embodiments, the protein is a therapeutic protein. In certain embodiments, the protein is an enzyme (e.g., hydrolase, kinase, phosphorylase, cytochrome p450 enzyme, protease, polymerase, aldolase, ligase, phosphatase, etc.). In other embodiments, the protein is involved in a cell signaling pathway. In certain embodiments, the protein is a kinase. In certain embodiments, the protein is a transcription factor (e.g., NFκB, the Gli1 and Gli3 transcription factors of the Hedgehog pathway). In certain embodiments, the protein is a transmembrane signaling protein (e.g., Smoothened). In certain embodiments, the protein is a receptor. In other embodiments, the protein is a structural protein (e.g., tubulin, myosin, actin, etc.) The target protein preferably has a biological activity that is disrupted when the intein-ligand binding domain is inserted into the target protein. Once the intein is removed by the protein splicing activity of the intein itself, the protein's biological activity is restored. In sum, a hybrid protein containing a ligand-dependent intein is inactive until the ligand which binds to the intein is added. The ligand binding restores the protein splicing activity of the intein, which cause the excision of the intein and ligation of the resulting ends to form the mature, biologically active target protein.

In order to evolve a ligand-dependent intein from an intein-ligand binding domain construct, the construct is inserted in frame into the open reading frame of a target protein. Preferably, the activity of the target protein is one which can be easily detected, selected, or screened for. For example, cells may rely on the target protein's activity to divide. Or, the spliced protein may be easily detectable because it is fluorescent (e.g., green fluorescent protein (GFP)). The construct may be inserted into a target sequence using any methods known in the art. The sequence of the target protein may be mutated to introduce restriction sites for inserting the intein construct in frame. Optionally, linkers may be used to insert the intein construct into the target protein's sequence. In certain embodiments, standard cloning techniques are used to insert the construct into the target protein sequence. In certain embodiments, the polymerase chain reaction (PCR) may be used in preparing the construct. The resulting hybrid protein with the construct inserted has the general structure:

Target (N)-Intein (N)-Ligand Binding Domain-Intein (C)-Target (C) wherein the intein construct with the ligand binding domain is flanked by N-terminal and C-terminal portions of the target protein. The intein construct may also be at the N- or C-terminus of the target protein.

The construct encoding the hybrid protein with the intein inserted is used to transform cells. In certain embodiments, the intein-ligand binding domain encoding polynucleotide sequence is mutated (e.g., using error-prone PCR (Cadwell et al. *PCR Methods Appl.* 2:28, 1992; incorporated herein by reference), site-directed mutagenesis, etc.), and the resulting library of constructs inserted into a target protein is transformed into cells. In certain embodiments, just the sequence encoding the ligand binding domain is mutated. In other embodiments, just the sequence encoding the intein is mutated. In certain embodiments, the sequences of the exteins flanking the ligand-dependent intein are mutated. These cells may be grown under conditions to select for the vector encoding the hybrid protein. The cells are also grown under conditions that select for the active, mature protein both in the presence of and in the absence of the ligand. Without the ligand, the cells should not grow. With the ligand, the cells grow based on the activity of the target protein. For example, the target protein may confer antibiotic resistance (e.g, geneticin resistance). In the absence of the ligand, the target protein activity is disrupted by the intein, and the cells cannot grow in the presence of geneticin. With the ligand present, the intein gains its protein splicing activity, and the intein excises itself from the target protein restoring the activity of the target protein. Therefore, cells can grow in media containing geneticin in the presence of the ligand.

In selecting ligand-dependent inteins from a library of mutants, the positive clones may be picked, and optionally characterized, followed by subsequent rounds of screening and/or selection. This iterative process may be repeated using both positive selection as described above and/or using negative selection, positive screening, and/or negative screening. The negative screen or selection identifies ligand-dependent inteins which exhibit minimal background protein splicing in the absence of ligand. The process may be repeated any number of times to achieve the desired level of ligand dependency. In certain embodiments, there is only one round of screening or selection. In other embodiments, there are one, two, three, four, or five round of screening or selection. Preferably, there are at least two or three rounds of screening. In subsequent rounds of screening, clones are chosen and mutated using techniques such as error-prone PCR. These mutated clones are then screened, and second round clones are chosen. These second round clones may also be put through successive rounds of mutation followed by screening or selection. The selected clones may optionally be characterized, for example, by sequencing the clone, structural studies of the encoded protein, ligand binding assays, activity assays, etc.

One of the advantages of using ligand-dependent inteins as a method of modulating protein activity is that one ligand-dependent intein can be used in a variety of target protein contexts. Therefore, a different intein does not need to be developed for each protein to be studied. In Example 1 below, a 4-hydroxytamoxifen-dependent intein based on the *Mycobacterium tuberculosis* RecA intein is prepared using the ligand-binding domain from the human estrogen receptor. The developed intein was put through three rounds of selection and screening in order to achieve the desired level of intein activity and minimal background splicing. The intein was then shown to perform in a variety of extein contexts (e.g., green fluorescent protein, KanR, LacZ, and Ade2p.

Ligand-dependent inteins can be used to modulate target protein activity in vivo. The constructs containing the target protein with a ligand-dependent intein can be introduced into any type of cell. Examples of cells useful in the inventive system include bacterial (e.g., *E. coli*), fungal, yeast (e.g., *S. cerevisiae*, *S. pombe*, *Pichia pastoris*), nematodes (e.g., *C. elegans*), insect cells, and mammalian cells (e.g., human, monkey, rat, mouse).

Use of Ligand-Dependent Inteins

A hybrid protein, which includes a ligand-dependent intein inserted into a target protein, may be used to investigate the activity of a protein of interest or the role of a protein of interest in vivo. Ligand-dependent inteins provide a means of rapidly activating a protein by the addition of a ligand such as a small molecule. One can use this technology for investigating biochemical pathways, cell signaling pathways, developmental controls, etc. The construct may be transformed into any cell in which the activity of the protein is to be assessed. For example, if one were investigating the role of a particular transcription factor in mammalian cells, the construct would be used to transform mammalian cells. As described above, one of the advantages of ligand-dependent inteins is that once one is prepared, it may be used in a variety of extein contexts without further manipulation.

In other embodiments, the hybrid protein with the ligand-dependent intein is used for therapeutic purposes. The construct encoding the hybrid protein with the ligand-dependent intein inserted is administered to a subject or used to transformed cells which are subsequently administered to a subject. In certain embodiments, the construct is used to treat a particular disease. In other embodiments, the construct is used to prevent a disease. For example, the ligand, which activates the intein, may be found in a particular cell, tissue, and organ so that protein splicing only takes place in that cell, tissue, or organ. In other embodiments, the ligand-dependent intein may provide temporal control of the target protein's activity. That is, the ligand, which activates the intein, may only be provided exogenously or endogenously at a particular time. For example, the ligand may be a metabolite or waste product which is only produced at a certain time. Or the ligand may only be found in the cell during a particular part of the cell cycle. The inventive system may be used to treat cancer, autoimmune diseases, infectious diseases, heart disease, genetic diseases, neurological diseases, etc.

In order for one to use the inventive system, the polynucleotide encoding a ligand-dependent intein may be provided in a kit with accompanying instructions for its use. The kit may also include other polynucleotides, vectors, cells, buffers, enzymes, nucleotides, tubes, plates, ligand, maps, sequences, etc. for practicing the claimed invention. In certain embodiments, the kit provides many of the materials necessary for inserting the ligand-dependent intein into a target protein for further study. In other embodiments, the kit may include a polynucleotide encoding a hybrid protein. In certain embodiments, the kit provides many of the materials necessary for using a ligand-dependent intein therapeutically.

These and other aspects of the present invention will be further appreciated upon consideration of the following Examples, which are intended to illustrate certain particular embodiments of the invention but are not intended to limit its scope, as defined by the claims.

EXAMPLES

Example 1

Directed Evolution of Ligand Dependence: Small-Molecule-Activated Protein Splicing Materials and Methods Molecular Biology Reagents. Restriction enzymes, Vent DNA polymerase, and T4 DNA ligase were purchased from New England Biolabs. Oligonucleotides were synthesized by using an ABI Expedite 8909 DNA synthesizer. Geldanamycin (GDA), cycloheximide, and 4-hydroxytamoxifen (4-HT) were purchased from Sigma.

Yeast Strains and Standard Methods. *S. cerevisiae* strain 1284 (leu2-3,112 ura3-52 his3-Δ200 lys2-801 trpl -Δ901 suc2-Δ9) was used for the geneticin-resistance selection and in screening the GFP libraries. Strain 1285 (ade2-101, leu2-3,112 ura3-52 his3-Δ200 trpl -Δ901 suc2-Δ9) was used in the Ade2 experiments. Strain RDY96 (erg6Δ::TRPl pdr1Δ::KanMX pdr3::HIS3 ade2-1 trpl -1 his3-11,15 ura3-52 leu2-3,112 can1-100) was used in the LacZ experiments and for the individual clone GFP flow cytometry and Western blot results reported (see FIGS. 2-4). Cultures were grown at 30° C. in yeast extract/peptone/dextrose (YPD) or complete synthetic medium lacking either tryptophan or uracil to maintain plasmids.

KanR Selection Plasmid. Standard cloning methods were used to assemble the KanR selection cassette, which contains the following components: (i) the N-terminal sequence of KanR res-idues 1-118, followed by (ii) the N-terminal 1-94 residues of the *M. tuberculosis* RecA intein, (iii) the LBD of the human estrogen receptor (ER), residues 304-551, (iv) the C-terminal intein sequence residues 383-440, and (v) residues 120-270 of the KanR protein. Residues 118 and 120 in the KanR protein were mutated to introduce cloning sites such that following splicing residues 118-120 are Ala-Cys-Arg. The sequences GPGGSG and SAGSGG were used as linkers between the intein(N) and ER LBD and between the ER LBD and intein(C) fragments, respectively. The sequence of the RecA intein with the ligand binding domain of ER inserted in place of the RecA endonuclease domain with two six amino acid linkers (underlined) in between is as follows:

(SEQ ID NO: 1)
CLAEGTRIFDPVTGTTHRIEDVVDGRKPIHVVAAAKDGTLHARPVVSWFD

QGTRDVIGLRIAGGAIVWATPDHKVLTEYGWRAAGELRKGDRVA<u>GPGGSG</u>

NSLALSLTADQMVSALLDAEPPILYSEYDPTRPFSEASMMGLLTNLADRE

LVHMINWAKRVPGFVDLTLHDQVHLLECAWLEILMIGLVWRSMEHPGKLL

FAPNLLLDRNQGKCVEGMVEIFDMLLATSSRFRMMNLQGEEFVCLKSIIL

-continued

LNSGVYTFLSSTLKSLEEKDHIHRVLDKITDTLIHLMAKAGLTLQQQHQR

LAQLLLILSHIRHMSNKRMEHLYSMKCKNVVPLYDLLLEMLDAHRLHAGG

SGASRVQAFADALDDKFLHDMLAEELRYSVIREVLPTRRARTFDLEVEEL

HTLVAEGVVVHN

Figure 1A:
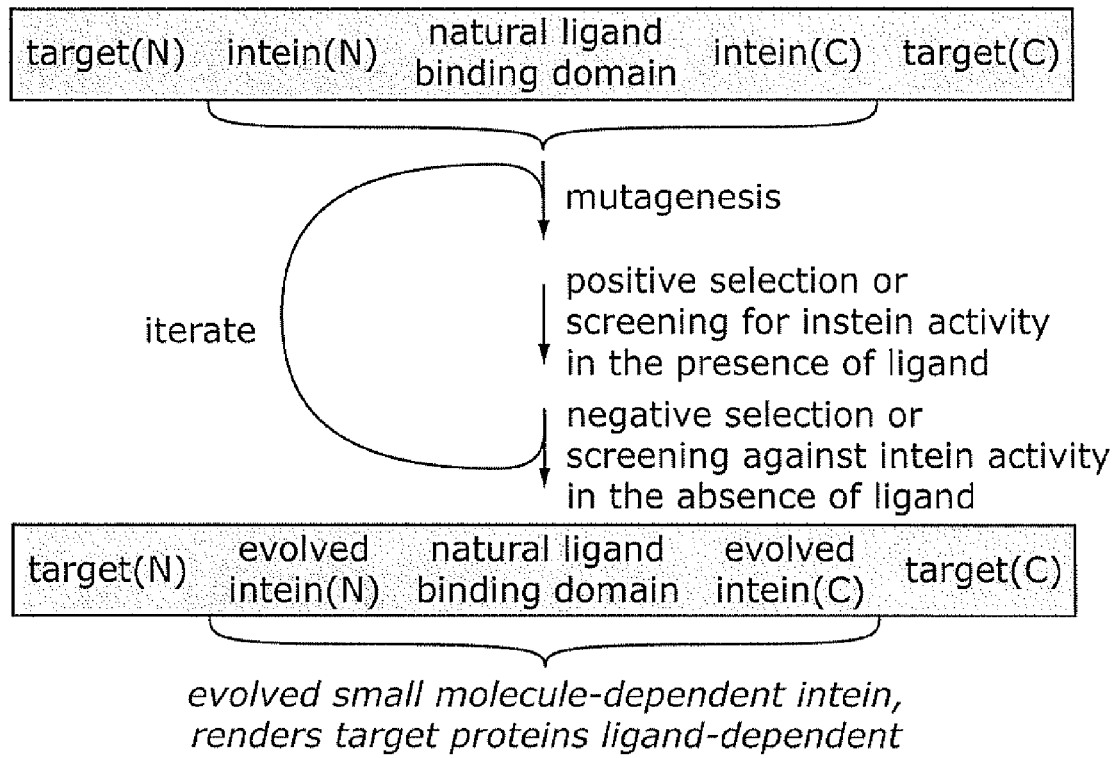
FIG. 1 shows the inventive approach of evolving a ligand-dependent intein and results involving the KanR protein. (A) Strategy for the directed evolution of a ligand-dependent intein. (B) Intein-ER fusion clones 1-1 and 1-14 were inserted into the kanamycin-resistance protein (KanR) at position 119. *S. cerevisiae* cells expressing these constructs were plated on medium containing 150 µg/ml geneticin in the presence or absence of 10 µM 4-HT.

Genes encoding KanR and the RecA intein were obtained by PCR from pACYC177 (New England Biolabs) and pMU1B (Shingledecker et al. (1998) *Gene* 207, 187-195; incorporated herein by reference), respectively. The ER-LBD sequence from pCMVCre-ER(T) (Feil et al. (1996) *Proc. Natl. Acad. Sci. USA* 93, 10887-10890; incorporated herein by reference) contains the mutation G521R and binds 4-HT but not p-estradiol. The construct encoding KanR(N)-intein (N)-ER LBD-intein(C)-KanR(C) (FIG. 1A) was amplified by PCR and cloned into the yeast expression vector p424GPD (Mumberg et al. (1995) *Gene* 156, 119-122; incorporated herein by reference) (from American Type Culture Collection). This selection was based on the work of Daugelat and Jacobs (Daugelat et al. (1999) *Protein Sci.* 8, 644-653; incorporated herein by reference), who linked intein splicing to kanamycin resistance in *Escherichia coli.*

GFP Screen Development. Umezawa and coworkers (Ozawa et al. (2001) *Anal. Chem.* 73, 5866-5874; incorporated herein by reference) previously reported linking intein splicing to GFP fluorescence by fusing the N- and C-terminal halves of the split intein from Ssp DnaE to halves of GFP and interacting partners such as M13 and calmodulin. They report that when M13 and calmodulin interact, the GFP(N)-intein (N)-calmodulin and M13-intein(C)-GFP(C) proteins associate, and following intein folding and splicing, GFP fluorescence is restored. They inserted the intein fragments in a loop at residue 157 of GFP. Based on this precedent, we cloned WT RecA intein into this position of GFP(uv) (Crameri et al. (1996) *Nat. Biotechnol.* 14, 315-319; incorporated herein by reference), driven by the pBAD promoter in *Escherichia coli.* Surprisingly, we found that both the WT intein and an inactive intein mutant in which the necessary C-terminal Cys was mutated to Ala yielded a high degree of fluorescence at 25° C. (as visualized by long-wave UV and by flow cytometry). These results suggest that intein splicing is not required for GFP folding and that simple protein-protein association of the intein halves was responsible for fluorescence. We therefore sought to create a system that linked intein splicing (rather than split intein association) to GFP fluorescence and after analysis of the crystal structure (Ormo et al. (1996) *Science* 273, 1392-1395; incorporated herein by reference) inserted the intein at residue 108 of GFP as described below (see also FIG. 7).

GFP Screening Plasmid. DNA encoding residues 107-109 of GFP [with mutations Phe-64→Leu and Ser-65Thr→(Cormack et al. (1996) *Gene* 173, 33-38; incorporated herein by reference) added to GFP(uv)] was replaced with a construct encoding Ala-intein-Arg that leaves an Ala-Cys-Arg scar after splicing. To create a yeast expression vector for the GFP-intein construct, we cloned the DNA encoding the GFP/wild-type intein fusion described above into p414GAL1 (Mumberg et al. (1994) *Nucleic Acids Res.* 22, 5767-5768; incorporated herein by referencee). Genes encoding inteins containing the ER LBD were subcloned into this GFP construct.

Vectors Expressing Intein-LacZ and Intein-Ade2p. In vivo homologous recombination of overlapping PCR fragments was used to insert DNA encoding intein clone 3-2 into the lacZ gene. Amino acids 437-439 of LacZ were replaced with Ala-intein-Arg; after splicing, residues 437-439 become Ala-Cys-Arg. The x-ray crystal structure of LacZ (Jucrs et al. (2000) *Protein Sci.* 9, 1685-1699; incorporated herein by reference) indicates that this site lies in the middle of an a-helix in the central α/β-barrel. DNA encoding this intein-LacZ fusion was cloned into p416GAL1 and introduced into RDY96.

Homologous recombination of overlapping PCR fragments was used to insert intein 3-2 into position 422 of the endogenous ADE2 gene. In this case, no postsplicing scar remains, because restriction sites are not necessary for cloning and position 422 is naturally cysteine. This position is predicted to lie in an essential a-helix by analysis of the crystal structure of the homologous *E. coli* protein PurE (Mathews et al. (1999) *Struct. Fold. Des.* 7, 1395-1406; incorporated herein by reference). The intein-Ade2p construct was cloned into p416GAL1 and introduced into strain 1285.

Figure 1B:
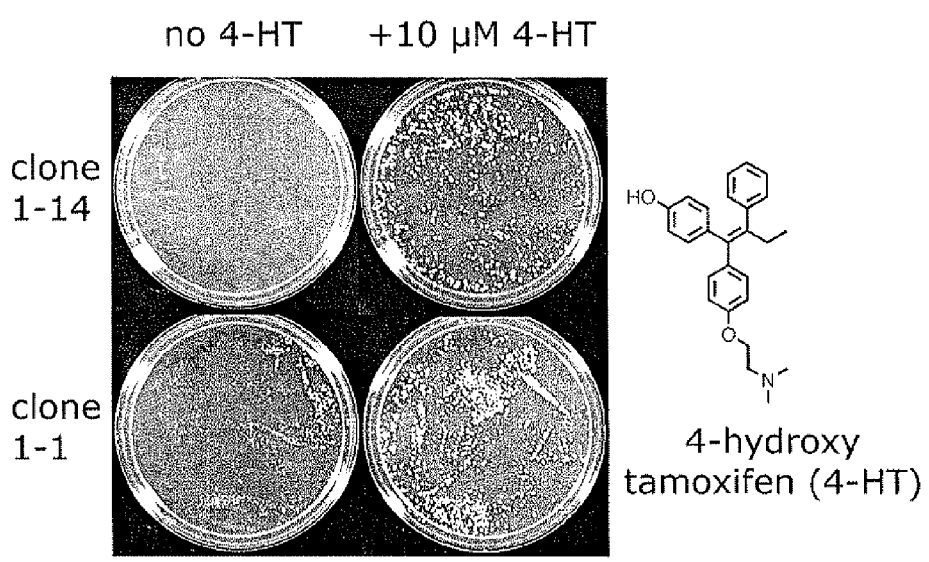

Selection for Geneticin Resistance (Round One). Point mutations were introduced into the gene encoding the intein-ER fusion described above by using error-prone PCR (Cadwell et al. (1994) *PCR Methods Appl.* 3, 5136-S140; incorporated herein by reference). The mutant intein library was ligated into the p424GPD-KanR selection vector; XL-1 blue cells (Stratagene) were transformed with this library, yielding an initial complexity of 1×10⁷ transformants. The plasmid library was amplified in XL-1 blue cells in 400 ml of 2×yeast-tryptone+100 μg/ml ampicillin and then trans-formed into *S. cerevisiae* strain 1284 (6×10⁵ transformants). The yeast library was grown for 4 h in YPD medium containing 10 μM 4-HT and plated on YPD medium containing 150 μg/ml geneticin and 10 μM 4-HT. Survivors were grown in medium lacking tryptophan and induced in YPD with 4-HT before replating (FIG. 1B).

Analysis of Round One Mutations. An intein mutation found in clone 1-1 (Val-67→Leu) was characterized by Belfort and coworkers (Wood et al. (1999) *Nat. Biotechnol.* 17, 889-892; incorporated herein by reference) and found to increase the activity and temperature stability of minimal splicing domains of the RecA intein. Three other clones acquired estrogen receptor ligand-binding domain (ER-LBD) mutations that likely disrupt the interaction of helix 12 with the rest of the ER LBD: clone 1-5 contains a mutation at Tyr-537, a residue in helix 12 shown to be crucial for helix 12 packing (White et al. (1997) *EMBO J.* 16, 1427-1435; incorporated herein by reference), and clones 1-14 and 1-16 both acquired Val-376→Ala substitutions. Val-376 participates in a significant hydrophobic interaction with the conserved LXXLL motif in helix 12 (Shiau et al. (1998) *Cell* 95, 927-937; incorporated herein by reference). We speculate that its mutation to Ala disrupts this interaction, allowing the flanking intein domains to adopt a conformation more amenable to protein splicing. Last, clone 1-14 also acquired an Arg-521→Gly mutation that has been reported (Nichols et al. (1998) *EMBO J.* 17, 765-773; incorporated herein by reference) to increase 4-hydroxytamoxifen (4-HT) affinity≈100-fold.

Fluorescence-Based Positive and Negative Screen (Round Two). Point mutations were introduced into genes encoding inteins 1-14 and 1-1 by error-prone PCR. The resulting library was ligated into the GFP selection vector and transformed into *E. coli* (initial complexity of 1×10⁷ transformants). After amplification, the plasmid library was transformed into *S. cerevisiae* strain 1284 (2×10⁶ transformants). The yeast library was grown in 30 ml of medium lacking tryptophan for 24 h and diluted into fresh medium containing galactose and 4-HT to induce protein expression and intein splicing. After 24 hours, the culture was sorted by using a MoFlo fluorescence-activated cell-sorting (FACS) instrument (Cytomation, Fort Collins, Colo.). Of $2.4 \times 10^7$ cells screened, those exceeding 100-fold fluorescence ($\approx 5 \times 10^5$ cells) above background were collected and regrown in medium lacking tryptophan. This constitutes the first positive screen.

When this culture reached saturation, the cells were washed and grown for 24 h in fresh medium lacking tryptophan and 4-HT and containing galactose. This culture was sorted for the lack of fluorescence in the absence of 4-HT (the negative screen). Cells ($6 \times 10^5$ of $5.5 \times 10^6$ screened) with <10-fold fluorescence relative to background were collected and regrown. This cycle of positive and negative screening of the library was repeated once more, and individual clones arising from the third positive GFP screen included clones 2-4 and 2-5.

The p414GAL1-based GFP selection vector was lost from cells at a high rate leading to bimodal fluorescence distributions. Switching to a URA3 marker (p416GAL1) and using strain RDY96 better maintained the plasmid and increased the intra-cellular concentration of 4-HT. The FACS and Western blot data shown in FIG. 2 were collected by using this superior vector and strain system. Loss of plasmid was only solved completely by integrating the GFP-intein construct containing clone 3-2 into the genome at the URA3 locus in RDY96, as was done for the FACS and Western blot data shown in FIGS. 3 and 4.

Figure 3A:
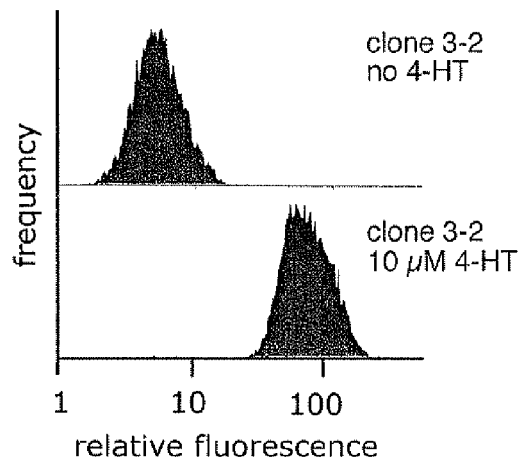
FIG. 3 demonstrates how evolved ligand-dependent intein 3-2 modulates protein function in living cells in four contexts. (A) FACS analysis of yeast expressing intein 3-2 inserted into GFP after 24 hours of growth in the presence or absence of 4-HT. The gene encoding the intein-GFP construct was integrated into yeast genomic DNA to preclude loss of the construct. (B) Intein 3-2 inserted into the KanR context was plated on medium containing 100 µg/ml geneticin in the presence or absence of 4-HT. (C) Yeast expressing LacZ containing intein 3-2 were grown 16 hours with or without 4-HT and assayed for β-galactosidase activity (Pryciak et al. *Mol. Cell. Biol.* 16:2614-26, 1996; incorporated herein by reference) in triplicate. LacZ activities are normalized relative to the same yeast strain lacking the lacZ gene. (D) Yeast expressing intein 3-2 inserted into the endogenous *S. cerevisiae* protein Ade2p were plated on medium containing 10 mg/liter adenine in the presence or absence of 4-HT and compared with an ade2⁻ strain. Yeast lacking Ade2p activity accumulate a red pigment; colonies with Ade2p activity maintain their white color.
Figure 3B:
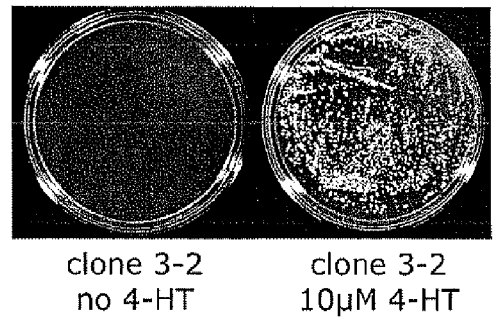

Selection for Increased Intein Activity (Round Three). Plasmids from clones 2-4 and 2-5 were used as templates for a third round of error-prone PCR under conditions that allow recombination (template swapping). The resulting DNA was cloned into the KanR selection vector, yielding a library in $E.$ $coli$ of $4 \times 10^6$ transformants, and in yeast strain 1284 of $2 \times 10^6$ transformants. The yeast library was plated on YPD medium containing 150 μg/ml geneticin and 10 μM 4-HT. More than 1,000 survivors were harvested. The surviving intein-ER-encoding DNA was cloned en masse into the p416GAL1-GFP selection vector, yielding an $E. coli$ library of $5 \times 10^6$ transformants. Plasmids purified from this library were used to transform strain RDY96 ($1 \times 10^4$ transformants). This yeast library was grown in medium lacking uracil containing 10 μM 4-HT and sorted via FACS; cells with >50-fold fluorescence above background were collected ($\approx 2 \times 10^5$ of $4 \times 10^6$ screened). Analysis of individual clones highlighted 3-2, which showed increased GFP fluorescence in the presence of 4-HT compared with its parental clones while maintaining no detectable fluorescence in the absence of ligand. Subcloning into the KanR selection vector and plating on YPD medium containing 100 μg/ml geneticin and 10 μM 4-HT confirmed that its splicing activity is sufficient to confer geneticin resistance (FIG. 3B).

Analysis of Round Two and Three Mutations. To elucidate the mutations responsible for small-molecule-dependent splicing in intein 3-2, we generated a series of site-directed mutants of its evolutionary ancestors. First we examined the relative importance of the two ER mutations acquired by clone 1-14 (grandparent of clone 3-2): Val-376→Ala and Arg-521→Gly. The Val-376→Ala mutation alone was sufficient to confer resistance in the KanR context to 200 μg/ml geneticin in the presence of 4-HT, although growth is less robust than with the additional Arg-521→Gly mutation. In contrast, the single Arg-521→Gly mutant is unable to survive in the KanR context on 200 μg/ml geneticin. The Val-376→Ala mutation therefore is the primary contributor to the increased activity of clone 1-14.

To determine the role of the mutations acquired in clone 2-4 (a descendent of 1-14 and a parent of 3-2), we introduced the intein His-41→Leu mutation into 1-14 in the GFP context, creating the triple mutant. Analysis of the fluorescence properties of this minimal 2-4 clone showed that it is phenotypically indistinguishable from clone 2-4. We conclude that the other ER mutations in clone 2-4 do not contribute appreciably to the activity or ligand dependence. We then added the Ala-34→Val mutant to this triple mutant, now in the KanR context, creating the minimal 3-2 intein (Ala-34→Val and His-41→Leu in the intein; Val-376→Ala and Arg-521→Gly in the ER LBD). Although the triple mutant mentioned above (minimal 2-4) in the KanR context is unable to confer geneticin resistance at 75 μg/ml geneticin, similar to the 2-4 clone itself, the quadruple mutant (minimal 3-2) is sufficiently active in the presence of 4-HT to grow under these conditions. We conclude that the Ala-34→Val mutation enhances the activity of the His-41→Leu mutation inherited from 2-4 and increases activity (possibly through improved folding in the ligand-bound state) without increasing the ligand-independent background. Analysis of the homologous Ssp DnaB intein structure (Ding et al. (2003) $J. Biol. Chem.$ 278, 39133-39142; incorporated herein by reference) suggests that the side chains of these two residues are in close proximity in the tertiary structure of the intein, consistent with this hypothesis.

Assays for LacZ and Ade2p Activity. To evaluate ligand-dependent LacZ activity, cultures were grown in medium lacking uracil, containing galactose, and containing either no 4-HT or 10 μM 4-HT. The cells were lysed after 16 h and assayed for β-galactosidase activity as described (Pryciak et al. (1996) $Mol. Cell. Biol.$ 16, 2614-2626; incorporated herein by reference). RDY96 lacking the lacZ gene was grown on medium lacking tryptophan and analyzed in parallel as a negative control.

Yeast strain 1285 containing the intein-Ade2p fusion was plated on medium containing 2% galactose, 1% raffinose, no uracil, and 10 mg/liter adenine with or without 10 μM 4-HT. Cells were grown for 90 h. Cells containing the p416GAL1 plasmid (lacking any ADE2 gene) were plated under the same conditions as a control to ensure that 4-HT does not affect cell color.

Probing the Role of Hsp90 with GDA. GDA binds to the ATPase site of Hsp90 and inhibits its function (Prodromou et al. (1997) $Cell$ 90, 65-75; incorporated herein by reference). Cultures of RDY96 with an integrated GFP-intein 3-2 were grown in the presence or absence of 10 μM 4-HT for 20 hours, and ligand-dependent splicing was compared by Western blot with cultures grown in the presence of 10 GDA with or without 10 μM 4-HT. To uncouple steady-state protein synthesis and degradation, we inhibited translation by treating a 16-h culture with 100 μg/ml cycloheximide for 1 hour, after which 10 μM GDA was added, and protein splicing at 0, 2, and 6 h after GDA addition was observed.

Results and Discussion

Round One: Evolution of Active Intein-ER Fusions. The human ER LBD (residues 304-551) binds ligands including the synthetic small molecule 4-HT with high affinity. After 4-HT binding, helix 12 is thought to undergo a major conformational shift that reduces the separation of the N and C termini of the ER LBD (Shiau et al. (1998) $Cell$ 95, 927-937; incorporated herein by reference). We replaced the dispensable homing endonuclease domain (Wood et al. (1999) $Nat.$ $Biotechnol.$ 17, 889-892; incorporated herein by reference) of the RecA intein with the ER LBD, yielding a 424-residue intein(N)-ER-intein(C) fusion. To assay splicing of this construct in vivo, we linked protein splicing to antibiotic resistance in $S. cerevisiae.$ Insertion of the wild-type RecA intein (but not a mutant intein containing an essential Cys-to-Ala substitution) at residue 119 of aminoglycoside phosphorylase (KanR) (Daugelat et al. (1999) *Protein Sci.* 8, 644-653; incorporated herein by reference) enables *S. cerevisiae* cells to grow robustly in the presence of the antibiotic geneticin. In contrast, the intein(N)-ER-intein(C) construct, when inserted into KanR at the same position (FIG. 1A), confers no geneticin resistance in the presence or absence of 4-HT (FIG. 6). Simple insertion of the ER LBD into the RecA intein therefore does not result in ligand-dependent protein splicing but rather causes the loss of splicing activity.

To restore intein activity, we generated a library of point-mutated intein(N)-ER-intein(C) genes ($6 \times 10^5$ transformants) by using error-prone PCR (Cadwell et al. (1994) *PCR Methods Appl.* 3, 5136-S140; incorporated herein by reference) and selected yeast cells expressing the library in the presence of 4-HT and geneticin. Forty colonies survived this positive selection (round one, Table 1), suggesting that their splicing activity was restored. These clones were screened for sensitivity to geneticin in the absence of 4-HT. Six clones exhibited robust geneticin resistance in the presence of 4-HT but reduced growth in its absence (FIG. 1B), suggestive of some degree of ligand-dependent splicing. DNA sequencing of round-one clones revealed mutations predicted to increase intein activity (Val-67→Leu in clone 1-1) (Wood et al. (1999) *Nat. Biotechnol.* 17, 889-892), disrupt the interaction of helix 12 with the rest of the ER LBD (such as Val-376→Ala in clone 1-14) (Shiau et al. (1998) *Cell* 95, 927-937; incorporated herein by reference), and increase ER affinity for 4-HT (Arg-521→Gly in 1-14) (Nichols et al. (1998) *EMBO J.* 17, 765-773; incorporated herein by reference) (see *Supporting Text*, which is published as supporting information on the PNAS web site). The role of these and other mutations acquired during intein evolution is discussed below.

TABLE 1

Mutations within evolved inteins

| Round-clone number | ER-LBD mutations | Intein mutations |
|---|---|---|
| 1-1 | — | V67L |
| 1-5 | V533E, Y537H | — |
| 1-14 | V376A, R521G | — |
| 1-16 | V376A | K394R, L396Q |
| 2-4 | R335S, C530Y, V478A, V376A, R521G | H41L |
| 2-5 | S468P, V376A, R521G | V31M, R416L |
| 3-2 | R335S, C530Y, V478A, V376A, R521G, K531T | A34V, H41L |
| Minimal 3-2 | V376A, R521G | A34V, H41L |

Round Two: Evolution of Ligand Dependence. Although the first round of mutagenesis and selection successfully restored intein activity in a partially ligand-dependent manner, round-one clones exhibited substantial background splicing in the absence of 4-HT (FIGS. 1B and 2A and B). To decrease ligand-independent background splicing, we developed a screen both for and against protein splicing by inserting the intein(N)-ER-intein(C) into *Aequorea victoria* GFP. Based on the work of Umezawa and coworkers (Ozawa et al. (2001) *Anal Chem.* 73, 5866-5874; incorporated herein by reference), we initially inserted the intein construct at residue 157 but found that splicing of the resulting protein was not required for fluorescence (see *Supporting Text*). We therefore altered the location of intein insertion to position 108 of GFP, which lies near the midpoint of a β-strand (Ormo et al. (1996) *Science* 273, 1392-1395; incorporated herein by reference), and verified that insertion of the wild-type RecA intein at this position abolishes fluorescence until protein splicing takes place (FIG. 7). The resulting intein-GFP construct formed the basis of a useful screen, because both active and inactive intein-encoding genes in this context could be isolated from mixed populations by FACS (see below). The GFP screen also enables small differences in intein activities to be detected, in contrast to the binary response of the KanR selection. Indeed, analysis of clone 1-14 in the GFP context revealed significant ligand-independent splicing (FIG. 2A) that was below the thresh-old of detection in the KanR selection (FIG. 1B).

Intein clones 1-14 and 1-1 were diversified by random point mutagenesis ($2 \times 10^6$ transformants) in the GFP context and screened for splicing activity in the presence of 4-HT (positive screen). Cells exhibiting strong fluorescence were collected and regrown in the absence of ligand. Nonfluorescent cells in the absence of 4-HT then were collected (negative screen). A total of three positive and two negative screens resulted in the evolution of round-two inteins with dramatically improved 4-HT dependence. Clones 2-4 and 2-5 each exhibited no detectable GFP fluorescence in the absence of ligand but significant fluorescence in the presence of 4-HT (FIG. 2A). Consistent with these results, Western blots revealed significant spliced GFP product in the presence of 4-HT but no detectable spliced protein in the absence of ligand (FIG. 2B).

Round Three: Evolution of Improved Ligand-Dependent Activity. Although these results indicated the successful evolution of a high degree of ligand dependence, the second-round inteins characterized possess less splicing activity when activated than their round-one parental clones. Indeed, inteins 2-4 and 2-5 in the KanR context failed to induce sufficient splicing in the presence of 4-HT to confer 100 µg/ml geneticin resistance. To improve splicing activity while maintaining the high degree of evolved ligand dependence, we generated a third library of inteins by point mutagenesis and recombination of clones 2-4 and 2-5. The resulting round-three library ($2 \times 10^6$ transformants) was selected in the KanR context for third-generation mutant inteins that confer geneticin resistance. Surviving clones were recloned into the GFP context and screened both for fluorescence in the presence of 4-HT and for nonfluorescence in the absence of 4-HT as described above. Clone 3-2 combined the strong activity of round-one clones with the strong ligand dependence of round-two clones. In the KanR context, clone 3-2 confers resistance to 100 µg/ml geneticin only in the presence of 4-HT (FIG. 3B). Importantly, no splicing by FACS or Western blot analysis was observed in the GFP context (FIGS. 3A and 4A) in the absence of 4-HT, indicating that ligand-independent splicing is very low.

To elucidate the mutations responsible for small-molecule-dependent splicing in intein 3-2, we generated a series of site-directed mutants of its evolutionary ancestors (clones 1-14 and 2-4). The splicing activities and ligand dependencies of the resulting mutants (Table 1) in the KanR and GFP contexts indicate that four mutations (ER LBD: Val-376→Ala and Arg-521→Gly; intein: His-41→Leu and Ala-34→Val) are sufficient for highly ligand-dependent splicing activity. A minimal 3-2 intein containing only these four mutations is phenotypically indistinguishable from intein 3-2 in the KanR context.

Figure 3C:
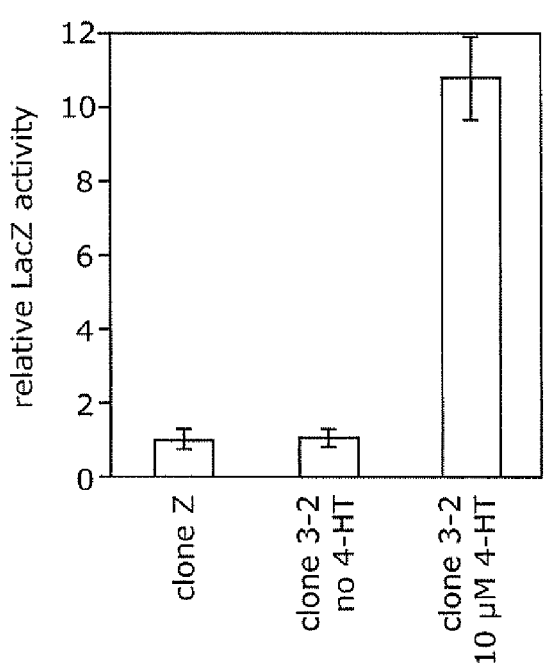

Generality, Splicing Kinetics, and Dependence on Ligand Dosage. The generality of ligand-dependent protein splicing by intein 3-2 was examined by introducing this evolved protein switch into two contexts that were not used during its evolution. Insertion at residue 438 of β-galactosidase (LacZ) places intein 3-2 in an a-helix within the central α/β-barrel of LacZ (Juers et al. (2000) *Protein Sci.* 9, 1685-1699; incorporated herein by reference). When expressed in yeast cells in the absence of 4-HT, the resulting protein does not generate β-galactosidase activity above that of negative control cells lacking the lacZ gene. After treatment with 4-HT, significant β-galactosidase activity is produced (FIG. 3C). The modest level of LacZ activity compared with that arising from expression of a wild-type lacZ gene may be caused by reduced expression or stability of the large intein-containing LacZ protein.

Figure 3D:
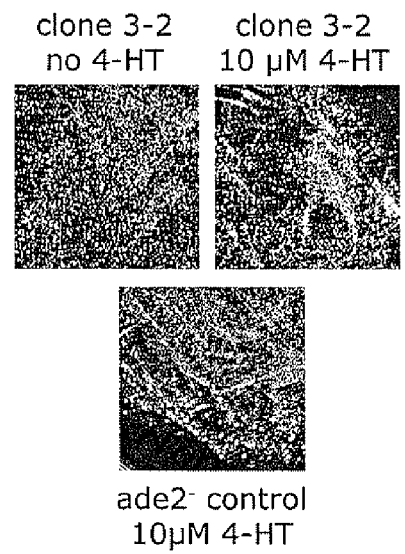

In addition, we studied the ability of intein 3-2 to render an endogenous *S. cerevisiae* protein dependent on 4-HT. Ade2p is required for the biosynthesis of adenine, and its absence results in a distinct red colony phenotype. Insertion of intein 3-2 at position 422 [predicted by homology with *E. coli* PurE (Mathews et al. (1999) *Struct. Fold. Des.* 7, 1395-1406; incorporated herein by reference) to be a-helical] abolishes Ade2p activity, resulting in red colonies comparable in color to that of a control strain lacking the ADE2 gene (FIG. 3D). In the presence of 4-HT, however, cells expressing the intein-Ade2p are white, indicating that Ade2p function is restored after small-molecule treatment (FIG. 3D). These results suggest that insertion of evolved intein 3-2 into arbitrary proteins of interest renders their function dependent on 4-HT.

Small-molecule-mediated approaches to modulating protein activity posttranslationally are of particular interest because of their superior kinetics and dose dependence compared with purely genetic approaches (Alaimo et al. (2001) *Curr. Opin. Chem. Biol.* 5, 360-367; incorporated herein by reference). To assess the kinetics of ligand-induced splicing mediated by clone 3-2, we followed the progress of protein splicing by Western blot in the GFP context. Yeast cells expressing intein 3-2-GFP in the absence of 4-HT were treated with 100 μg/ml cycloheximide for 1 h to prevent the translation of new protein. Before the addition of 4-HT, no splicing was detected. As early as 30 min after 4-HT treatment (the first time point), a significant fraction of the protein had spliced, and the majority of protein was spliced after several hours (FIG. 4A). In a control experiment treated with cycloheximide but lacking 4-HT, no splicing was observed over 8 hours (data not shown). Additional rounds of directed evolution using a kinetic selection may result in faster splicing variants. The observation of ligand-dependent splicing after cycloheximide treatment confirms that 4-HT treatment alters the structure of previously synthesized target protein posttranslationally.

Small-molecule dose dependence of splicing was characterized under equilibrium conditions by exposing intein 3-2 in the GFP context to different concentrations of 4-HT and analyzing the statistical distribution of spliced protein after 28 hours. FACS analysis revealed that for each concentration of 4-HT between 1 nM and 10 μM, cells are distributed statistically within a narrow fluorescence window that smoothly varies with the concentration of 4-HT (FIG. 4B). This graded small-molecule dose dependence contrasts with the response of most ligand-activated promoters (Siegele et al. (1997) *Proc. Natl. Acad. Sci. USA* 94, 8168-8172; incorporated herein by reference) that alter the ratios of fully induced and uninduced cells rather than the level of induced protein within each cell. Similar dose-dependent modulation of protein function has proven useful already in the elucidation of protein function by chemical genetic studies (Alaimo et al. (2001) *Curr. Opin. Chem. Biol.* 5, 360-367; incorporated herein by reference).

Models for Evolved Ligand Dependence. At least two models (not mutually exclusive) may explain the ligand dependence within the evolved inteins described above. In the first model, the Hsp90 complex known to associate with the ER LBD (Pratt et al. (1997) *Endocr. Rev.* 18, 306-360; incorporated herein by reference) prevents intein folding and splicing until 4-HT binding induces dissociation of the complex. In some previously reported ER fusions (Picard, (2000) *Methods Enzymol.* 327, 385-401; incorporated herein by reference), it is thought that Hsp90 acts by sterically blocking other macromolecules from associating with the fusion. Indeed, all the proteins that have been successfully rendered ligand-dependent by ER-LBD fusion involve the interaction between two macro-molecules: protein-DNA interaction in the case of transcription factors and protein-protein interaction in the case of kinases. In contrast, fusions of the ER LBD with enzymes that act on small molecules such as Ura3p, DHFR, and galactokinase do not confer ligand dependence (Picard, (2000) *Methods Enzymol.* 327, 385-401; incorporated herein by reference), presumably because Hsp90 association does not readily preclude the function of enzymes that do not need to associate with macromolecular substrates. Intein splicing is an intramolecular event that does not require the association of macromolecules and therefore is not expected to be rendered ligand-dependent by a steric occlusion mechanism. Consistent with this analysis, the inteins before round two exhibited poor ligand dependence despite their fusion with the ER LBD.

To further probe the possible role of Hsp90 in ligand-dependent splicing, we treated yeast cells expressing intein 3-2 in the GFP context with GDA, a small-molecule inhibitor of Hsp90 function. GDA treatment did not induce splicing of intein 3-2 in the absence of 4-HT (FIG. 4C, lane 3), suggesting that Hsp90 activity is not required for inhibition of splicing. To uncouple protein synthesis and degradation, we inhibited translation by treatment with 100 μg/ml cycloheximide for 1 hour, added GDA to 10 μM, and monitored splicing. As shown in FIG. 4C, lanes 5-7, no splicing is observed at 2 or 6 h in the absence of 4-HT, and by 6 h the prespliced construct has been degraded. These results are consistent with the hypothesis that Hsp90 is involved in enhancing intein-ER expression levels, possibly by stabilizing a partially unfolded protein, but is not solely responsible for ligand dependence.

We favor a second model in which the His-41→Leu mutation in clone 3-2 destabilizes productive intein folding, increasing the ability of the unliganded ER LBD to enforce an intein conformation that is inconsistent with splicing. In the presence of 4-HT, we speculate that conformational changes tuned by ER mutation Val-376→Ala and intein mutation Ala-34→Val restore intein structure to a state that undergoes efficient spontaneous splicing when the ER LBD is liganded. In support of this second model, the homologous Ssp DnaB intein structure (Ding et al. (2003) *J. Biol. Chem.* 278, 39133-39142; incorporated herein by reference) suggests that the side chains of intein residues 34 and 41 pack together and lie near the interface of the intein halves (FIG. 5). It is significant that the mutations that increase ligand dependence after round one arise in the intein, not in the ER LBD. We suggest that highly active inteins such as clone 1-1 fold favorably (Wood et al. (1999) *Nat. Biotechnol.* 17, 889-892; incorporated herein by reference), splice quickly, and are not significantly hindered by the ER-LBD conformation; in contrast, mutations in intein 3-2 create a destabilized intein conformation that permits regulation by the ER LBD. Because simple insertion of the ER LBD into the RecA intein did not yield ligand-dependent splicing activity, these mutations are necessary to optimize intein activity and enforce conformational changes that accurately transduce ligand binding into protein splicing.

In summary, we developed and implemented a directed-evolution strategy to generate an artificial protein molecular switch. Our findings collectively highlight the ability of an in vivo molecular evolution approach to generate and simultaneously maintain many complex and crucial properties including ligand affinity, protein expression, protein solubility, protein stability, and a high ratio of "on" to "off" protein activity. In the case of the RecA intein, this strategy successfully coupled the presence of a synthetic small molecule to protein splicing in a wide variety of contexts (α-helices in KanR, LacZ, and Ade2p and a β-sheet in GFP). These results are examples of using a small molecule to directly trigger a change in the primary structure and biological function of proteins in living cells. Inteins evolved in this work leave only a single Cys residue as a postsplicing scar and may serve as a general tool for activating protein function with the cell-permeable small-molecule 4-HT in a rapid, specific, post-translational, and dose-dependent manner that does not require the synthesis and discovery of new small molecules.

Example 2

Elucidation of the Mammalian Hedgehog Pathway Using a Ligand-Dependent Intein The generality of the ligand-dependent intein described in Example 1 (ER-intein), its speed of splicing in response to 4-HT, and its control at the post-translational level make it a valuable tool in the study of mammalian systems. One area in which it may prove particularly useful is in the study of developmental signaling pathways, in which the activation of certain proteins at specific times is responsible for important developmental events. One example of this type of signaling pathway is the Hedgehog pathway. Insertion of the ER-intein can provide control over a single component of this complex pathway, thus providing insight into how the pathway operates.

Figure 8B:
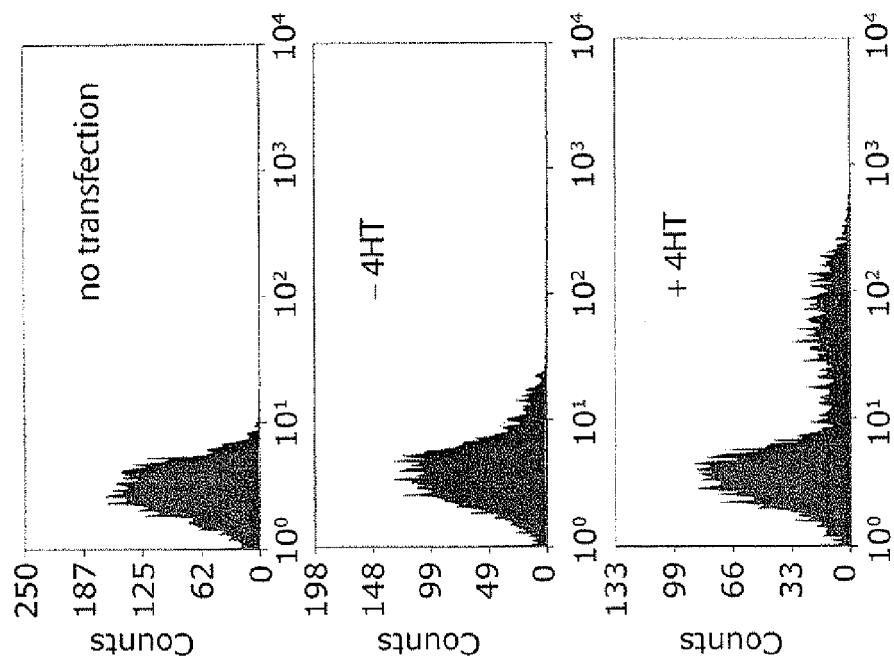
Figure 8A:
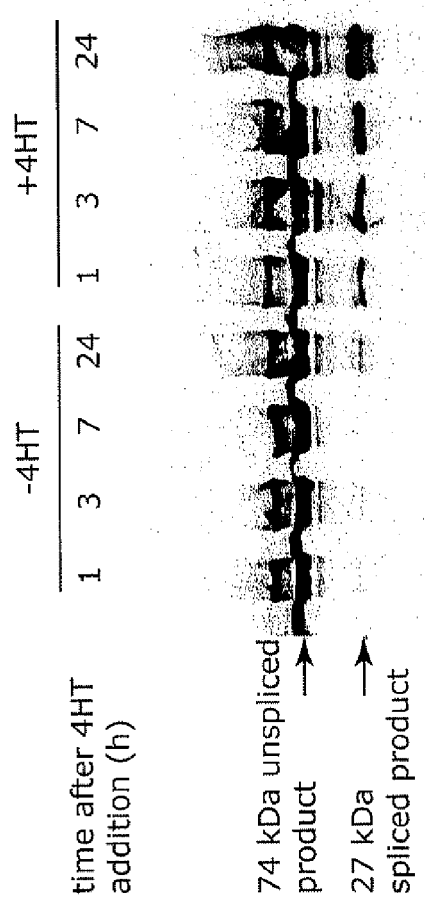

In order to realize this goal of using the ER-intein to study the Hedgehog pathway, it is necessary to show that the ER-intein construct shows the same ligand-dependent activity in mammalian cells that it does in yeast. A vector containing the ER-intein inserted into GFP was transiently transfected into Cos-7 cells. The ER-intein used in this construct (intein 2-4 in Example 1) was chosen over the more active intein 3-2 because the latter shows significant background splicing in the absence of 4-HT. Splicing was observed as early as 1 hour after addition of 4-HT (FIG. 8A). The spliced protein is active, as confirmed by both flow cytometric analysis and visualization under a fluorescence microscope (FIG. 8B). Flow cytometry data support the conclusion that 4-HT-dependent splicing is taking place.

Generation of a stable cell line containing ER-intein-GFP is possible. This cell line will be used to study the splicing kinetics and dose-dependence of the construct. A stable cell line will produce more informative flow cytometry data, as neither variation in transfection efficiency nor variation in copy number will be an issue. Candidates for ER-intein insertion are the Gli1 and Gli3 transcription factor of the Hedgehog pathway and the transmembrane signaling protein Smoothened.

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

SEQUENCE LISTING

```
<160> NUMBER OF SEQ ID NOS: 14

<210> SEQ ID NO 1
<211> LENGTH: 412
<212> TYPE: PRT
<213> ORGANISM: Artificial
<220> FEATURE:
<223> OTHER INFORMATION: M. tuberculosis RecA intein with the estrogen
      ligand binding domain inserted in place of the RecA endonuclease
      domain with six amino acid linkers in between.

<400> SEQUENCE: 1

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95
```

```
Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
            115                 120                 125

Asp Pro Thr Arg Pro Phe Ser Glu Ala Ser Met Met Gly Leu Leu Thr
            130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Val His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
            195                 200                 205

Arg Asn Gln Gly Lys Cys Val Glu Gly Met Val Glu Ile Phe Asp Met
210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Val Leu Asp Lys Ile Thr Asp Thr Leu Ile His Leu Met Ala
            275                 280                 285

Lys Ala Gly Leu Thr Leu Gln Gln Gln His Gln Arg Leu Ala Gln Leu
            290                 295                 300

Leu Leu Ile Leu Ser His Ile Arg His Met Ser Asn Lys Arg Met Glu
305                 310                 315                 320

His Leu Tyr Ser Met Lys Cys Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
            355                 360                 365

His Asp Met Leu Ala Glu Glu Leu Arg Tyr Ser Val Ile Arg Glu Val
            370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn
                405                 410

<210> SEQ ID NO 2
<211> LENGTH: 94
<212> TYPE: PRT
<213> ORGANISM: Artificial
<220> FEATURE:
<223> OTHER INFORMATION: N-terminal portion of M. tuberculosis RecA
      intein.

<400> SEQUENCE: 2

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
```

-continued

```
                35                   40                  45
Phe Asp Gln Gly Thr Arg Asp Val Ile Gly Leu Arg Ile Ala Gly Gly
         50                   55                  60

Ala Ile Val Trp Ala Thr Pro Asp His Lys Val Leu Thr Glu Tyr Gly
 65                  70                  75                  80

Trp Arg Ala Ala Gly Glu Leu Arg Lys Gly Asp Arg Val Ala
                 85                  90

<210> SEQ ID NO 3
<211> LENGTH: 6
<212> TYPE: PRT
<213> ORGANISM: Artificial
<220> FEATURE:
<223> OTHER INFORMATION: Linker sequence.

<400> SEQUENCE: 3

Gly Pro Gly Gly Ser Gly
1               5

<210> SEQ ID NO 4
<211> LENGTH: 248
<212> TYPE: PRT
<213> ORGANISM: Artificial
<220> FEATURE:
<223> OTHER INFORMATION: Ligand binding domain of human estrogen
      receptor.

<400> SEQUENCE: 4

Asn Ser Leu Ala Leu Ser Leu Thr Ala Asp Gln Met Val Ser Ala Leu
1               5                   10                  15

Leu Asp Ala Glu Pro Pro Ile Leu Tyr Ser Glu Tyr Asp Pro Thr Arg
                20                  25                  30

Pro Phe Ser Glu Ala Ser Met Met Gly Leu Leu Thr Asn Leu Ala Asp
            35                  40                  45

Arg Glu Leu Val His Met Ile Asn Trp Ala Lys Arg Val Pro Gly Phe
        50                  55                  60

Val Asp Leu Thr Leu His Asp Gln Val His Leu Leu Glu Cys Ala Trp
 65                  70                  75                  80

Leu Glu Ile Leu Met Ile Gly Leu Val Trp Arg Ser Met Glu His Pro
                85                  90                  95

Gly Lys Leu Leu Phe Ala Pro Asn Leu Leu Leu Asp Arg Asn Gln Gly
                100                 105                 110

Lys Cys Val Glu Gly Met Val Glu Ile Phe Asp Met Leu Leu Ala Thr
            115                 120                 125

Ser Ser Arg Phe Arg Met Met Asn Leu Gln Gly Glu Glu Phe Val Cys
        130                 135                 140

Leu Lys Ser Ile Ile Leu Leu Asn Ser Gly Val Tyr Thr Phe Leu Ser
145                 150                 155                 160

Ser Thr Leu Lys Ser Leu Glu Glu Lys Asp His Ile His Arg Val Leu
                165                 170                 175

Asp Lys Ile Thr Asp Thr Leu Ile His Leu Met Ala Lys Ala Gly Leu
            180                 185                 190

Thr Leu Gln Gln Gln His Gln Arg Leu Ala Gln Leu Leu Leu Ile Leu
        195                 200                 205

Ser His Ile Arg His Met Ser Asn Lys Arg Met Glu His Leu Tyr Ser
    210                 215                 220

Met Lys Cys Lys Asn Val Val Pro Leu Tyr Asp Leu Leu Leu Glu Met
225                 230                 235                 240
```

Leu Asp Ala His Arg Leu His Ala
            245

<210> SEQ ID NO 5
<211> LENGTH: 6
<212> TYPE: PRT
<213> ORGANISM: Artificial
<220> FEATURE:
<223> OTHER INFORMATION: Linker sequence.

<400> SEQUENCE: 5

Gly Gly Ser Gly Ala Ser
1               5

<210> SEQ ID NO 6
<211> LENGTH: 58
<212> TYPE: PRT
<213> ORGANISM: Artificial
<220> FEATURE:
<223> OTHER INFORMATION: C-terminal portion of M. tuberculosis RecA
      intein.

<400> SEQUENCE: 6

Arg Val Gln Ala Phe Ala Asp Ala Leu Asp Asp Lys Phe Leu His Asp
1               5                   10                  15

Met Leu Ala Glu Glu Leu Arg Tyr Ser Val Ile Arg Glu Val Leu Pro
            20                  25                  30

Thr Arg Arg Ala Arg Thr Phe Asp Leu Glu Val Glu Glu Leu His Thr
        35                  40                  45

Leu Val Ala Glu Gly Val Val Val His Asn
    50                  55

<210> SEQ ID NO 7
<211> LENGTH: 412
<212> TYPE: PRT
<213> ORGANISM: Artificial
<220> FEATURE:
<223> OTHER INFORMATION: Round 1 ligand-dependent intein derived from
      SEQ ID NO: 1.

<400> SEQUENCE: 7

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Arg Pro Phe Ser Glu Ala Ser Met Met Gly Leu Leu Thr
    130                 135                 140

Asn Leu Ala Asp Arg Glu Leu Val His Met Ile Asn Trp Ala Lys Arg

```
                145                 150                 155                 160
Val Pro Gly Phe Val Asp Leu Thr Leu His Asp Gln Val His Leu Leu
                165                 170                 175
Glu Cys Ala Trp Leu Glu Ile Leu Met Ile Gly Leu Val Trp Arg Ser
                180                 185                 190
Met Glu His Pro Gly Lys Leu Leu Phe Ala Pro Asn Leu Leu Leu Asp
                195                 200                 205
Arg Asn Gln Gly Lys Cys Val Glu Gly Met Val Glu Ile Phe Asp Met
                210                 215                 220
Leu Leu Ala Thr Ser Ser Arg Phe Arg Met Met Asn Leu Gln Gly Glu
225                 230                 235                 240
Glu Phe Val Cys Leu Lys Ser Ile Ile Leu Leu Asn Ser Gly Val Tyr
                245                 250                 255
Thr Phe Leu Ser Ser Thr Leu Lys Ser Leu Glu Glu Lys Asp His Ile
                260                 265                 270
His Arg Val Leu Asp Lys Ile Thr Asp Thr Leu Ile His Leu Met Ala
                275                 280                 285
Lys Ala Gly Leu Thr Leu Gln Gln Gln His Gln Arg Leu Ala Gln Leu
                290                 295                 300
Leu Leu Ile Leu Ser His Ile Arg His Met Ser Asn Lys Arg Met Glu
305                 310                 315                 320
His Leu Tyr Ser Met Lys Cys Lys Asn Val Val Pro Leu Tyr Asp Leu
                325                 330                 335
Leu Leu Glu Met Leu Asp Ala His Arg Leu His Ala Gly Gly Ser Gly
                340                 345                 350
Ala Ser Arg Val Gln Ala Phe Ala Asp Ala Leu Asp Asp Lys Phe Leu
                355                 360                 365
His Asp Met Leu Ala Glu Glu Leu Arg Tyr Ser Val Ile Arg Glu Val
                370                 375                 380
Leu Pro Thr Arg Arg Ala Arg Thr Phe Asp Leu Glu Val Glu Glu Leu
385                 390                 395                 400
His Thr Leu Val Ala Glu Gly Val Val Val His Asn
                405                 410

<210> SEQ ID NO 8
<211> LENGTH: 412
<212> TYPE: PRT
<213> ORGANISM: Artificial
<220> FEATURE:
<223> OTHER INFORMATION: Round 1 ligand-dependent intein derived from
      SEQ ID NO: 1.

<400> SEQUENCE: 8

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
                20                  25                  30

Ala Ala Ala Lys Asp Gly Thr Leu His Ala Arg Pro Val Val Ser Trp
                35                  40                  45

Phe Asp Gln Gly Thr Arg Asp Val Ile Gly Leu Arg Ile Ala Gly Gly
            50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95
```

-continued

```
Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Arg Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Val His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Val Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Arg Met Glu
305                 310                 315                 320

His Leu Tyr Ser Met Lys Cys Lys Asn Glu Val Pro Leu His Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Glu Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn
                405                 410
```

<210> SEQ ID NO 9
<211> LENGTH: 412
<212> TYPE: PRT
<213> ORGANISM: Artificial
<220> FEATURE:
<223> OTHER INFORMATION: Round 1 ligand-dependent intein derived from
      SEQ ID NO: 1.

<400> SEQUENCE: 9

```
Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45
```

Phe Asp Gln Gly Thr Arg Asp Val Ile Gly Leu Arg Ile Ala Gly Gly
        50                  55                  60

Ala Ile Val Trp Ala Thr Pro Asp His Lys Val Leu Thr Glu Tyr Gly
 65              70                  75                  80

Trp Arg Ala Ala Gly Glu Leu Arg Lys Gly Asp Arg Val Ala Gly Pro
             85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Arg Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Val Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Cys Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Glu Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn
                405                 410

<210> SEQ ID NO 10
<211> LENGTH: 412
<212> TYPE: PRT
<213> ORGANISM: Artificial
<220> FEATURE:
<223> OTHER INFORMATION: Round 1 ligand-dependent intein derived from
      SEQ ID NO: 1.

-continued

```
<400> SEQUENCE: 10

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Arg Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Val Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Arg Met Glu
305                 310                 315                 320

His Leu Tyr Ser Met Lys Cys Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Arg Phe Gln
        355                 360                 365

His Asp Met Leu Ala Glu Glu Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn
                405                 410
```

<210> SEQ ID NO 11
<211> LENGTH: 412
<212> TYPE: PRT
<213> ORGANISM: Artificial
<220> FEATURE:
<223> OTHER INFORMATION: Round 2 ligand-dependent intein derived from SEQ ID NO: 1.

<400> SEQUENCE: 11

```
Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
```

```
                355                 360                 365
His Asp Met Leu Ala Glu Glu Leu Arg Tyr Ser Val Ile Arg Glu Val
        370                 375                 380
Leu Pro Thr Arg Arg Ala Arg Thr Phe Asp Leu Glu Val Glu Glu Leu
385                 390                 395                 400
His Thr Leu Val Ala Glu Gly Val Val His Asn
                405                 410

<210> SEQ ID NO 12
<211> LENGTH: 412
<212> TYPE: PRT
<213> ORGANISM: Artificial
<220> FEATURE:
<223> OTHER INFORMATION: Round 2 ligand-dependent intein derived from
      SEQ ID NO: 1.

<400> SEQUENCE: 12

Cys Leu Ala Glu Gly Thr Arg Ile Phe Asp Pro Val Thr Gly Thr Thr
1               5                   10                  15
His Arg Ile Glu Asp Val Val Asp Gly Arg Lys Pro Ile His Met Val
            20                  25                  30
Ala Ala Ala Lys Asp Gly Thr Leu His Ala Arg Pro Val Val Ser Trp
        35                  40                  45
Phe Asp Gln Gly Thr Arg Asp Val Ile Gly Leu Arg Ile Ala Gly Gly
    50                  55                  60
Ala Ile Val Trp Ala Thr Pro Asp His Lys Val Leu Thr Glu Tyr Gly
65                  70                  75                  80
Trp Arg Ala Ala Gly Glu Leu Arg Lys Gly Asp Arg Val Ala Gly Pro
                85                  90                  95
Gly Gly Ser Gly Asn Ser Leu Ala Leu Ser Leu Thr Ala Asp Gln Met
            100                 105                 110
Val Ser Ala Leu Leu Asp Ala Glu Pro Pro Ile Leu Tyr Ser Glu Tyr
        115                 120                 125
Asp Pro Thr Arg Pro Phe Ser Glu Ala Ser Met Met Gly Leu Leu Thr
    130                 135                 140
Asn Leu Ala Asp Arg Glu Leu Val His Met Ile Asn Trp Ala Lys Arg
145                 150                 155                 160
Val Pro Gly Phe Val Asp Leu Thr Leu His Asp Gln Ala His Leu Leu
                165                 170                 175
Glu Cys Ala Trp Leu Glu Ile Leu Met Ile Gly Leu Val Trp Arg Ser
            180                 185                 190
Met Glu His Pro Gly Lys Leu Leu Phe Ala Pro Asn Leu Leu Leu Asp
        195                 200                 205
Arg Asn Gln Gly Lys Cys Val Glu Gly Met Val Glu Ile Phe Asp Met
    210                 215                 220
Leu Leu Ala Thr Ser Ser Arg Phe Arg Met Met Asn Leu Gln Gly Glu
225                 230                 235                 240
Glu Phe Val Cys Leu Lys Ser Ile Ile Leu Leu Asn Ser Gly Val Tyr
                245                 250                 255
Thr Phe Leu Ser Ser Thr Leu Lys Pro Leu Glu Glu Lys Asp His Ile
            260                 265                 270
His Arg Val Leu Asp Lys Ile Thr Asp Thr Leu Ile His Leu Met Ala
        275                 280                 285
Lys Ala Gly Leu Thr Leu Gln Gln Gln His Gln Arg Leu Ala Gln Leu
    290                 295                 300
```

```
Leu Leu Ile Leu Ser His Ile Arg His Met Ser Asn Lys Gly Met Glu
305                 310                 315                 320

His Leu Tyr Ser Met Lys Cys Lys Asn Val Val Pro Leu Tyr Asp Leu
            325                 330                 335

Leu Leu Glu Met Leu Asp Ala His Arg Leu His Ala Gly Gly Ser Gly
        340                 345                 350

Ala Ser Arg Val Gln Ala Phe Ala Asp Ala Leu Asp Asp Lys Phe Leu
    355                 360                 365

His Asp Met Leu Ala Glu Glu Leu Arg Tyr Ser Val Ile Arg Glu Val
        370                 375                 380

Leu Pro Thr Leu Arg Ala Arg Thr Phe Asp Leu Glu Val Glu Glu Leu
385                 390                 395                 400

His Thr Leu Val Ala Glu Gly Val Val Val His Asn
                405                 410

<210> SEQ ID NO 13
<211> LENGTH: 412
<212> TYPE: PRT
<213> ORGANISM: Artificial
<220> FEATURE:
<223> OTHER INFORMATION: Round 3 ligand-dependent intein derived from
      SEQ ID NO: 1.

<400> SEQUENCE: 13

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Val Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255
```

```
Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
            275                 280                 285

Lys Ala Gly Leu Thr Leu Gln Gln His Gln Arg Leu Ala Gln Leu
            290                 295                 300

Leu Leu Ile Leu Ser His Ile Arg His Met Ser Asn Lys Gly Met Glu
305                 310                 315                 320

His Leu Tyr Ser Met Lys Tyr Thr Asn Val Val Pro Leu Tyr Asp Leu
            325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
            355                 360                 365

His Asp Met Leu Ala Glu Glu Leu Arg Tyr Ser Val Ile Arg Glu Val
            370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn
            405                 410

<210> SEQ ID NO 14
<211> LENGTH: 412
<212> TYPE: PRT
<213> ORGANISM: Artificial
<220> FEATURE:
<223> OTHER INFORMATION: Round 3 ligand-derived intein derived from SEQ
      ID NO: 1 which is phenotypically indistinguishable from intein 3-2
      but with only four mutations.

<400> SEQUENCE: 14

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Val Ala Lys Asp Gly Thr Leu Leu Ala Arg Pro Val Val Ser Trp
            35                  40                  45

Phe Asp Gln Gly Thr Arg Asp Val Ile Gly Leu Arg Ile Ala Gly Gly
            50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
            85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
            115                 120                 125

Asp Pro Thr Arg Pro Phe Ser Glu Ala Ser Met Met Gly Leu Leu Thr
            130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
            165                 170                 175

Glu Cys Ala Trp Leu Glu Ile Leu Met Ile Gly Leu Val Trp Arg Ser
            180                 185                 190
```

```
Met Glu His Pro Gly Lys Leu Leu Phe Ala Pro Asn Leu Leu Leu Asp
    195             200             205

Arg Asn Gln Gly Lys Cys Val Glu Gly Met Val Glu Ile Phe Asp Met
    210             215             220

Leu Leu Ala Thr Ser Ser Arg Phe Arg Met Met Asn Leu Gln Gly Glu
225             230             235             240

Glu Phe Val Cys Leu Lys Ser Ile Ile Leu Leu Asn Ser Gly Val Tyr
            245             250             255

Thr Phe Leu Ser Ser Thr Leu Lys Ser Leu Glu Glu Lys Asp His Ile
            260             265             270

His Arg Val Leu Asp Lys Ile Thr Asp Thr Leu Ile His Leu Met Ala
        275             280             285

Lys Ala Gly Leu Thr Leu Gln Gln Gln His Gln Arg Leu Ala Gln Leu
    290             295             300

Leu Leu Ile Leu Ser His Ile Arg His Met Ser Asn Lys Gly Met Glu
305             310             315             320

His Leu Tyr Ser Met Lys Cys Lys Asn Val Val Pro Leu Tyr Asp Leu
                325             330             335

Leu Leu Glu Met Leu Asp Ala His Arg Leu His Ala Gly Gly Ser Gly
            340             345             350

Ala Ser Arg Val Gln Ala Phe Ala Asp Ala Leu Asp Asp Lys Phe Leu
        355             360             365

His Asp Met Leu Ala Glu Glu Leu Arg Tyr Ser Val Ile Arg Glu Val
    370             375             380

Leu Pro Thr Arg Arg Ala Arg Thr Phe Asp Leu Glu Val Glu Glu Leu
385             390             395             400

His Thr Leu Val Ala Glu Gly Val Val Val His Asn
                405             410
```

What is claimed is:

1. A method of producing and selecting a ligand-dependent intein, the method comprising the steps of:
    (a) providing a polynucleotide encoding a hybrid protein comprising a single polypeptide having a target protein with a ligand-dependent intein embedded in the sequence of said target protein, wherein said hybrid protein has the structure:

target(N)-Intein(N)-ligand binding domain-Intein(C)-target(C);

(b) mutating the sequence of the polynucleotide encoding the hybrid protein to generate a plurality of mutated polynucleotides;
    (c) transforming the polynucleotides produced in step (b) into cells;
    (d) selecting those cells having ligand-dependent intein activity based on the activity of the ligand-dependent intein in the presence of an appropriate ligand that binds the ligand binding domain, wherein a positive selection is based on the ability of the ligand-binding intein to excise itself from the target protein upon ligand binding and produce a functional target protein; and
    (e) optionally isolating the polynucleotides produced from the cells identified in step (d).

2. The method of claim 1, wherein the cells are bacterial cells.

3. The method of claim 1, wherein the cells are yeast cells.

4. The method of claim 1, wherein the cells are mammalian cells.

5. The method of claim 1, wherein the target protein without the ligand-dependent intein confers antibiotic resistance.

6. The method of claim 1, wherein the target protein without the ligand-dependent intein confers an ability to grow on a medium lacking a nutrient.

7. The method of claim 1, wherein the target protein without the ligand-dependent intein is fluorescent.

8. The method of claim 1, wherein the target protein without the ligand-dependent intein is an aminoglycoside phosphorylase.

9. The method of claim 1, wherein target protein without the ligand-dependent intein is β-galactosidase.

10. The method of claim 1, wherein the ligand is a small molecule.

11. The method of claim 1, wherein the ligand is 4-hydroxytamoxifen.

12. The method of claim 1, wherein the step of mutating comprises mutating polynucleotide sequence that encodes the ligand-dependent intein.

13. The method of claim 1, wherein the step of mutating comprises mutating the polynucleotide by error-prone polymerase chain reaction (PCR).

14. The method of claim 1, wherein the steps of mutating, transforming, and selecting are repeated to produce a ligand-dependent intein.

15. The method of claim 1, wherein the step of selecting is based on antibiotic resistance.

16. The method of claim 1, wherein the ligand-dependent intein has the structure:

intein(N-terminus)-ligand binding domain-intein (C-terminus)

whereby when the intein is inserted into a protein sequence, the intein exhibits minimal protein splicing activity in the absence of ligand.

17. The method of claim 1, wherein the ligand is selected from the group consisting of a small molecule, a peptide, a protein, a polynucleotide, an amino acid, a nucleotide, and combinations thereof.

18. The method of claim 1, wherein the ligand binding domain is derived from the ligand binding domain of the estrogen receptor.

19. The method of claim 1, wherein the N- and C-terminal portions of the intein are derived from the RecA intein of *Mycobacterium tuberculosis*.

20. The method of claim 1, wherein the N- and C-terminal portions of the intein are derived from the VMA intein of *Saccharomyces cerevisiae*.

21. The method of claim 1, wherein the intein has the primary amino acid sequence:

(SEQ ID NO: 1)
CLAEGTRIFDPVTGTTHRIEDVVDGRKPIHVVAAAKDGTLHARPVVSWFD

QGTRDVIGLRIAGGAIVWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQVHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNKRMEHLYSMKCKNVVPLYDLLLEMLDAHRLHAGG

SGASRVQAFADALDDKFLHDMLAEELRYSVIREVLPTRRARTFDLEVEEL

HTLVAEGVVVHN.

22. The method of claim 1, wherein the intein is at least 90% homologous to the sequence:

(SEQ ID NO: 1)
LAEGTRIFDPVTGTTHRIEDVVDGRKPIHVVAAAKDGTLHARPVVSWFDQ

GTRDVIGLRIAGGAIVWATPDHKVLTEYGWRAAGELRKGDRVAGPGGSGN

SLALSLTADQMVSALLDAEPPILYSEYDPTRPFSEASMMGLLTNLADREL

VHMINWAKRVPGFVDLTLHDQVHLLECAWLEILMIGLVWRSMEHPGKLLF

APNLLLDRNQGKCVEGMVEIFDMLLATSSRFRMMNLQGEEFVCLKSIILL

NSGVYTFLSSTLKSLEEKDHIHRVLDKITDTLIHLMAKAGLTLQQQHQRL

AQLLLILSHIRHMSNKRMEHLYSMKCKNVVPLYDLLLEMLDAHRLHAGGS

GASRVQAFADALDDKFLHDMLAEELRYSVIREVLPTRRARTFDLEVEELH

TLVAEGVVVHN.

23. The method of claim 1, wherein the intein is at least 95% homologous to the sequence:

(SEQ ID NO: 1)
CLAEGTRIFDPVTGTTHRIEDVVDGRKPIHVVAAAKDGTLHARPVVSWFD

QGTRDVIGLRIAGGAIVWATPDHKVLTEYGWRAAGELRKGDRVAGPGGSG

-continued

NSLALSLTADQMVSALLDAEPPILYSEYDPTRPFSEASMMGLLTNLADRE

LVHMINWAKRVPGFVDLTLHDQVHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNKRMEHLYSMKCKNVVPLYDLLLEMLDAHRLHAGG

SGASRVQAFADALDDKFLHDMLAEELRYSVIREVLPTRRARTFDLEVEEL

HTLVAEGVVVHN.

24. The method of claim 1, wherein the intein is at least 98% homologous to the sequence:

(SEQ ID NO: 1)
CLAEGTRIFDPVTGTTHRIEDVVDGRKPIHVVAAAKDGTLHARPVVSWFD

QGTRDVIGLRIAGGAIVWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQVHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNKRMEHLYSMKCKNVVPLYDLLLEMLDAHRLHAGG

SGASRVQAFADALDDKFLHDMLAEELRYSVIREVLPTRRARTFDLEVEEL

HTLVAEGVVVHN.

25. The method of claim 1, wherein the intein has the primary amino acid sequence selected from the group consisting of:

1-1:
(SEQ ID NO: 7)
CLAEGTRIFDPVTGTTHRIEDVVDGRKPIHVVAAAKDGTLHARPVVSWFD

QGTRDVIGLRIAGGAILWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQVHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNKRMEHLYSMKCKNVVPLYDLLLEMLDAHRLHAGG

SGASRVQAFADALDDKFLHDMLAEELRYSVIREVLPTRRARTFDLEVEEL

HTLVAEGVVVHN;

1-5:
(SEQ ID NO: 8)
CLAEGTRIFDPVTGTTHRIEDVVDGRKPIHVVAAAKDGTLHARPVVSWFD

QGTRDVIGLRIAGGAIVWATPDHKVLTEYGWRAAGELRKGDRVAGPGGSG

NSLALSLTADQMVSALLDAEPPILYSEYDPTRPFSEASMMGLLTNLADRE

LVHMINWAKRVPGFVDLTLHDQVHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRVLDKITDTLIHLMAKAGLTLQQQHQR

LAQLLLILSHIRHMSNKRMEHLYSMKCKNEVPLHDLLLEMLDAHRLHAGG

SGASRVQAFADALDDKFLHDMLAEELRYSVIREVLPTRRARTFDLEVEEL
HTLVAEGVVVHN;

1-14:

(SEQ ID NO: 9)
CLAEGTRIFDPVTGTTHRIEDVVDGRKPIHVVAAAKDGTLHARPVVSWFD
QGTRDVIGLRIAGGAIVWATPDHKVLTEYGWRAAGELRKGDRVAGPGGSG
NSLALSLTADQMVSALLDAEPPILYSEYDPTRPFSEASMMGLLTNLADRE
LVHMINWAKRVPGFVDLTLHDQAHLLECAWLEILMIGLVWRSMEHPGKLL
FAPNLLLDRNQGKCVEGMVEIFDMLLATSSRFRMMNLQGEEFVCLKSIIL
LNSGVYTFLSSTLKSLEEKDHIHRVLDKITDTLIHLMAKAGLTLQQQHQR
LAQLLLILSHIRHMSNKGMEHLYSMKCKNVVPLYDLLLEMLDAHRLHAGG
SGASRVQAFADALDDKFLHDMLAEELRYSVIREVLPTRRARTFDLEVEEL
HTLVAEGVVVHN 1-16:

(SEQ ID NO: 10)
CLAEGTRIFDPVTGTTHRIEDVVDGRKPIHVVAAAKDGTLHARPVVSWFD
QGTRDVIGLRIAGGAIVWATPDHKVLTEYGWRAAGELRKGDRVAGPGGSG
NSLALSLTADQMVSALLDAEPPILYSEYDPTRPFSEASMMGLLTNLADRE
LVHMINWAKRVPGFVDLTLHDQAHLLECAWLEILMIGLVWRSMEHPGKLL
FAPNLLLDRNQGKCVEGMVEIFDMLLATSSRFRMMNLQGEEFVCLKSIIL
LNSGVYTFLSSTLKSLEEKDHIHRVLDKITDTLIHLMAKAGLTLQQQHQR
LAQLLLILSHIRHMSNKRMEHLYSMKCKNVVPLYDLLLEMLDAHRLHAGG
SGASRVQAFADALDDRFQHDMLAEELRYSVIREVLPTRRARTFDLEVEEL
HTLVAEGVVVHN;

2-4:

(SEQ ID NO: 11)
CLAEGTRIFDPVTGTTHRIEDVVDGRKPIHVVAAAKDGTLLARPVVSWFD
QGTRDVIGLRIAGGAIVWATPDHKVLTEYGWRAAGELRKGDRVAGPGGSG
NSLALSLTADQMVSALLDAEPPILYSEYDPTSPFSEASMMGLLTNLADRE
LVHMINWAKRVPGFVDLTLHDQAHLLECAWLEILMIGLVWRSMEHPGKLL
FAPNLLLDRNQGKCVEGMVEIFDMLLATSSRFRMMNLQGEEFVCLKSIIL
LNSGVYTFLSSTLKSLEEKDHIHRALDKITDTLIHLMAKAGLTLQQQHQR
LAQLLLILSHIRHMSNKGMEHLYSMKYKNVVPLYDLLLEMLDAHRLHAGG
SGASRVQAFADALDDKFLHDMLAEELRYSVIREVLPTRRARTFDLEVEEL
HTLVAEGVVVHN;

2-5:

(SEQ ID NO: 12)
CLAEGTRIFDPVTGTTHRIEDVVDGRKPIHMVAAAKDGTLHARPVVSWFD
QGTRDVIGLRIAGGAIVWATPDHKVLTEYGWRAAGELRKGDRVAGPGGSG
NSLALSLTADQMVSALLDAEPPILYSEYDPTRPFSEASMMGLLTNLADRE
LVHMINWAKRVPGFVDLTLHDQAHLLECAWLEILMIGLVWRSMEHPGKLL
FAPNLLLDRNQGKCVEGMVEIFDMLLATSSRFRMMNLQGEEFVCLKSIIL
LNSGVYTFLSSTLKPLEEKDHIHRVLDKITDTLIHLMAKAGLTLQQQHQR
LAQLLLILSHIRHMSNKGMEHLYSMKCKNVVPLYDLLLEMLDAHRLHAGG
SGASRVQAFADALDDKFLHDMLAEELRYSVIREVLPTLRARTFDLEVEEL
HTLVAEGVVVHN;

3-2:

(SEQ ID NO: 13)
CLAEGTRIFDPVTGTTHRIEDVVDGRKPIHVVAVAKDGTLLARPVVSWFD
QGTRDVIGLRIAGGAIVWATPDHKVLTEYGWRAAGELRKGDRVAGPGGSG
NSLALSLTADQMVSALLDAEPPILYSEYDPTSPFSEASMMGLLTNLADRE
LVHMINWAKRVPGFVDLTLHDQAHLLECAWLEILMIGLVWRSMEHPGKLL
FAPNLLLDRNQGKCVEGMVEIFDMLLATSSRFRMMNLQGEEFVCLKSIIL
LNSGVYTFLSSTLKSLEEKDHIHRALDKITDTLIHLMAKAGLTLQQQHQR
LAQLLLILSHIRHMSNKGMEHLYSMKYTNVVPLYDLLLEMLDAHRLHAGG
SGASRVQAFADALDDKFLHDMLAEELRYSVIREVLPTRRARTFDLEVEEL
HTLVAEGVVVHN;

and

Min. 3-2:

(SEQ ID NO: 14)
CLAEGTRIFDPVTGTTHRIEDVVDGRKPIHVVAVAKDGTLLARPVVSWFD
QGTRDVIGLRIAGGAIVWATPDHKVLTEYGWRAAGELRKGDRVAGPGGSG
NSLALSLTADQMVSALLDAEPPILYSEYDPTRPFSEASMMGLLTNLADRE
LVHMINWAKRVPGFVDLTLHDQAHLLECAWLEILMIGLVWRSMEHPGKLL
FAPNLLLDRNQGKCVEGMVEIFDMLLATSSRFRMMNLQGEEFVCLKSIIL
LNSGVYTFLSSTLKSLEEKDHIHRVLDKITDTLIHLMAKAGLTLQQQHQR
LAQLLLILSHIRHMSNKGMEHLYSMKCKNVVPLYDLLLEMLDAHRLHAGG
SGASRVQAFADALDDKFLHDMLAEELRYSVIREVLPTRRARTFDLEVEEL
HTLVAEGVVVHN.

* * * * *